US009693706B2

(12) United States Patent
Shiodera et al.

(10) Patent No.: US 9,693,706 B2
(45) Date of Patent: Jul. 4, 2017

(54) IMAGE PROCESSING OF FLOWING FLUIDS WITHIN IMAGED ATONOMICAL STRUCTURE

(71) Applicant: Toshiba Medical Systems Corporation, Tochigi (JP)

(72) Inventors: Taichiro Shiodera, Tokyo (JP); Shuhei Nitta, Tokyo (JP); Tomoyuki Takeguchi, Kanagawa (JP); Nobuyuki Matsumoto, Tokyo (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 235 days.

(21) Appl. No.: 13/870,266

(22) Filed: Apr. 25, 2013

(65) Prior Publication Data
US 2013/0289387 A1     Oct. 31, 2013

(30) Foreign Application Priority Data

Apr. 27, 2012 (JP) ................................. 2012-103928
Mar. 25, 2013 (JP) ................................. 2013-062743

(51) Int. Cl.
| | | |
|---|---|---|
| *A61B 5/05* | (2006.01) | |
| *A61B 5/055* | (2006.01) | |
| *G01R 33/563* | (2006.01) | |
| *G06T 7/11* | (2017.01) | |
| *G01R 33/54* | (2006.01) | |

(52) U.S. Cl.
CPC ........ *A61B 5/055* (2013.01); *G01R 33/56308* (2013.01); *G06T 7/11* (2017.01); *A61B 2576/026* (2013.01); *G01R 33/546* (2013.01); *G06T 2207/30016* (2013.01)

(58) Field of Classification Search
USPC .......................................... 600/419
See application file for complete search history.

(56) References Cited

U.S. PATENT DOCUMENTS

| | | | |
|---|---|---|---|
| 8,823,376 B2 | 9/2014 | Yamashita et al. | |
| 9,042,961 B2 | 5/2015 | Miyazaki | |
| 2010/0087730 A1* | 4/2010 | Yamada et al. ............... | 600/419 |

(Continued)

FOREIGN PATENT DOCUMENTS

| | | |
|---|---|---|
| CN | 102028465 A | 4/2011 |
| JP | 2009-028525 | 2/2009 |

(Continued)

OTHER PUBLICATIONS

Yamada et al., Visualization of Cerebrospinal fluid movement with Spin Labeling at MR Imaging: Preliminary Results in Normal and Pathophysiologic Conditions. Radiology, vol. 249, No. 2, Nov. 2008, pp. 644-652.*

(Continued)

*Primary Examiner* — James Kish
(74) *Attorney, Agent, or Firm* — Nixon & Vanderhye P.C.

(57) ABSTRACT

An image processing apparatus according to an embodiment includes a specifying unit and a deriving unit. The specifying unit specifies a fluid region in a plurality of magnetic resonance images that are acquired by applying a labeling pulse to a label region and that are mutually related. The deriving unit derives an index indicating dynamics of a fluid on the basis of the specified fluid region.

17 Claims, 28 Drawing Sheets

(56) References Cited

U.S. PATENT DOCUMENTS

| | | | |
|---|---|---|---|
| 2010/0198053 A1* | 8/2010 | Miyazaki et al. | 600/419 |
| 2011/0037466 A1* | 2/2011 | Yamada et al. | 324/309 |
| 2011/0074416 A1 | 3/2011 | Yamashita et al. | |
| 2012/0095326 A1 | 4/2012 | Miyazaki | |

FOREIGN PATENT DOCUMENTS

| | | |
|---|---|---|
| JP | 2010-088515 | 4/2010 |
| JP | 2011-92670 A | 5/2011 |
| JP | 2012-81276 A | 4/2012 |

OTHER PUBLICATIONS

Shibuya et al., Pulsatile Cerebrospinal Fluid Flow Measurement Using Phase-Contrast Magnetic Resonance Imaging in Patients with Cervical Myelopathy. SPINE, vol. 27, No. 10, 20002. pp. 1087-1093.*

Kurtcuoglu et al., Computational Investigation of Subject-Specific Cerebrospinal Fluid Flow in the Third Ventricle and Aqueduct of Sylvius. Journal of Biomechanics, vol. 40, 2007, pp. 1235-1245.*

Office Action mailed Oct. 24, 2014, in CN 201310146770.2 with English translation.

Japanese Office Action dated Jan. 24, 2017 in JP 2013-062743.

\* cited by examiner

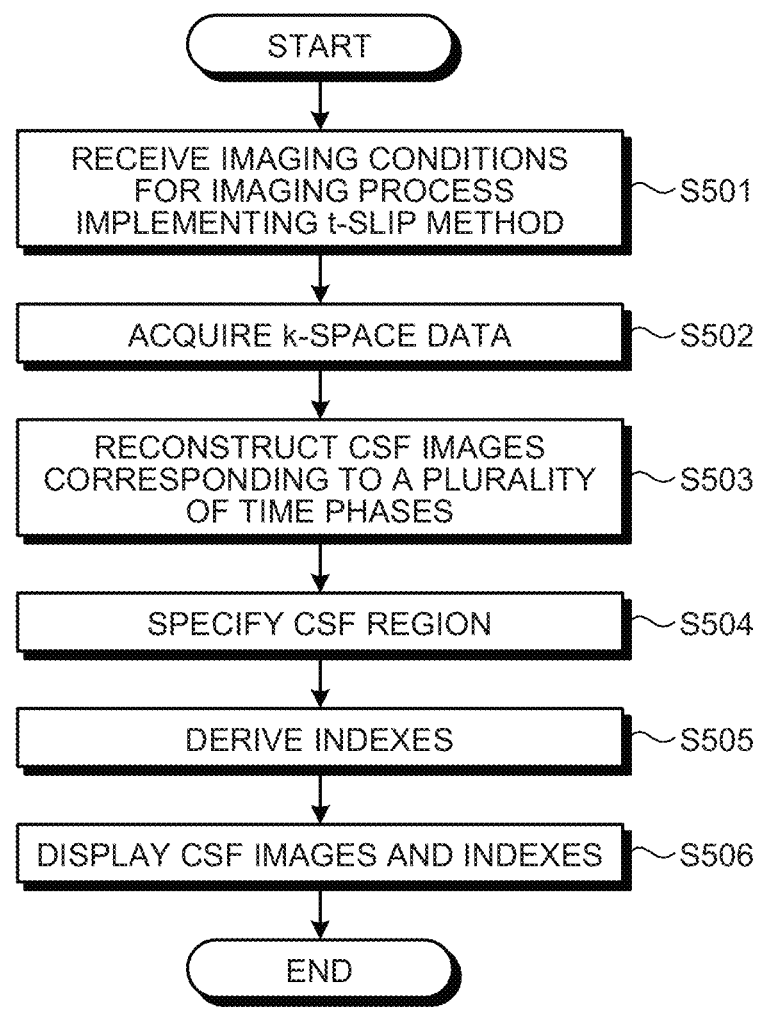

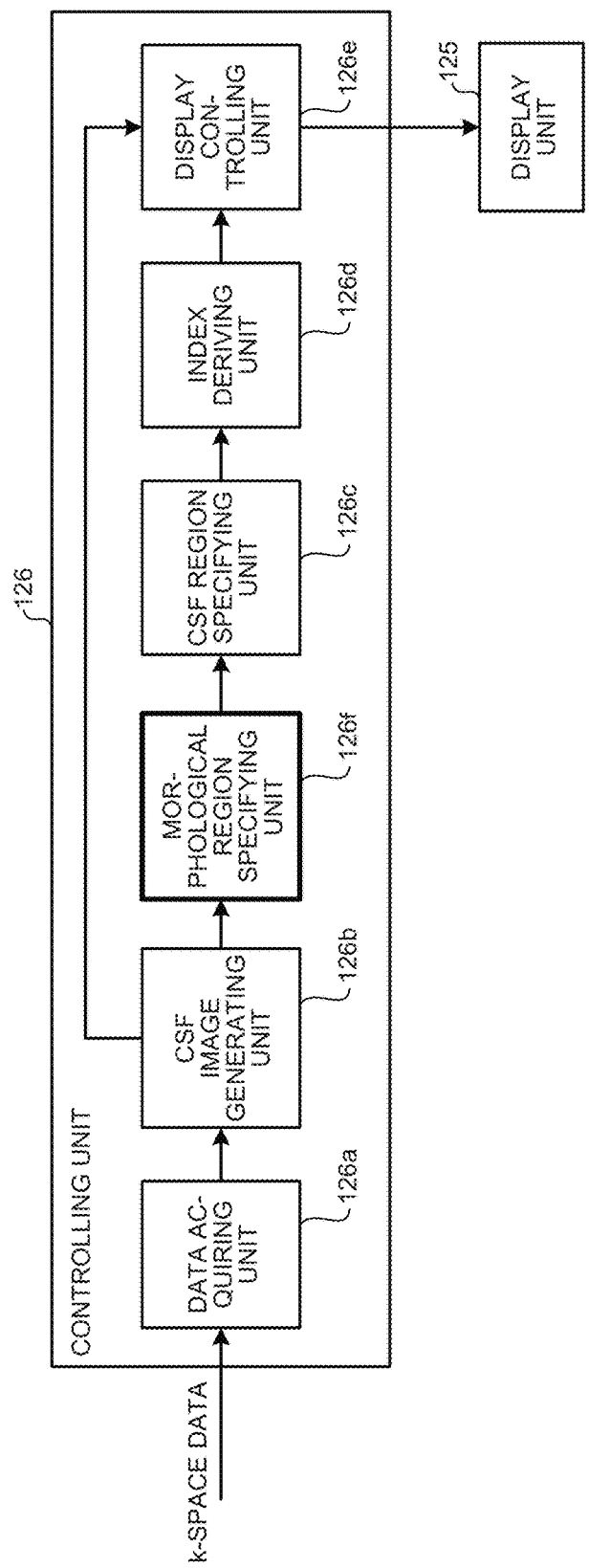

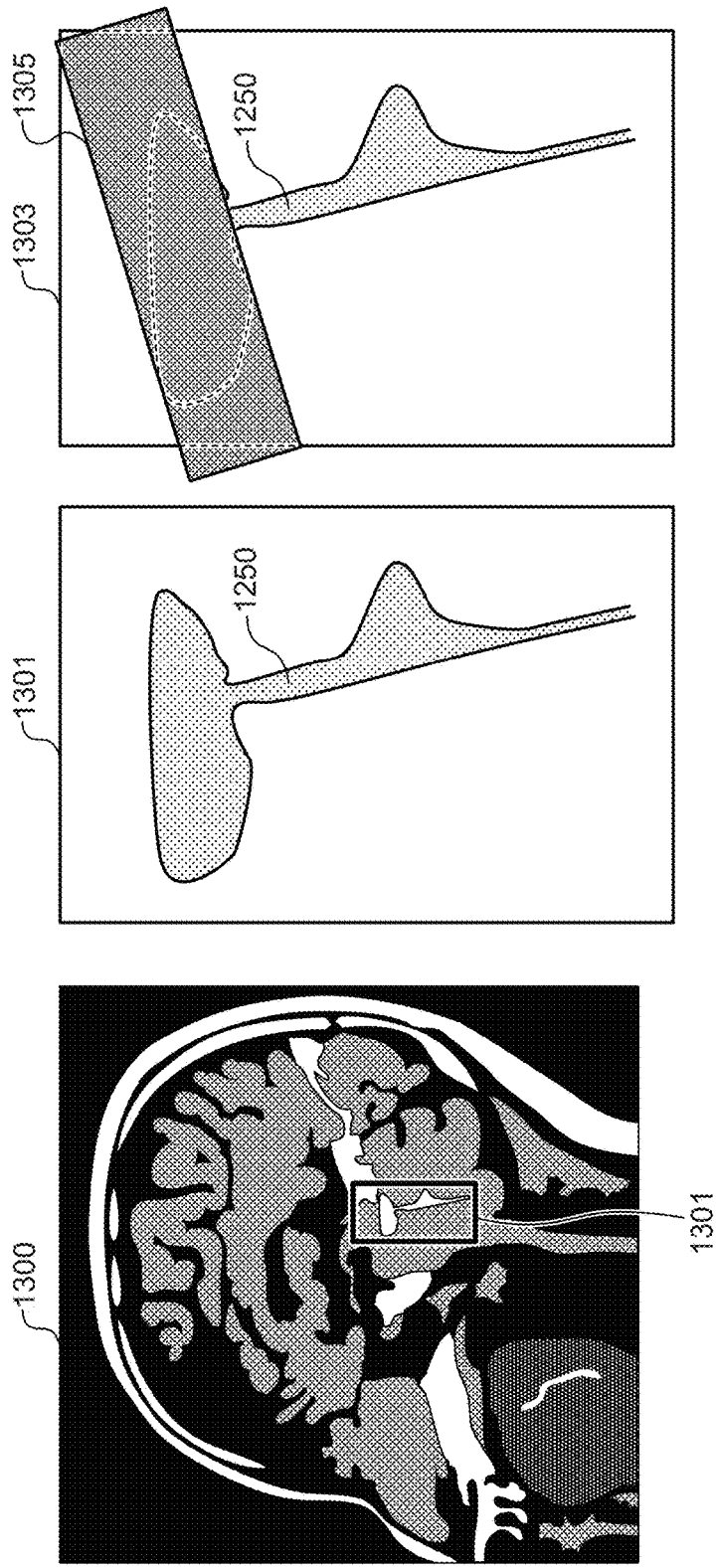

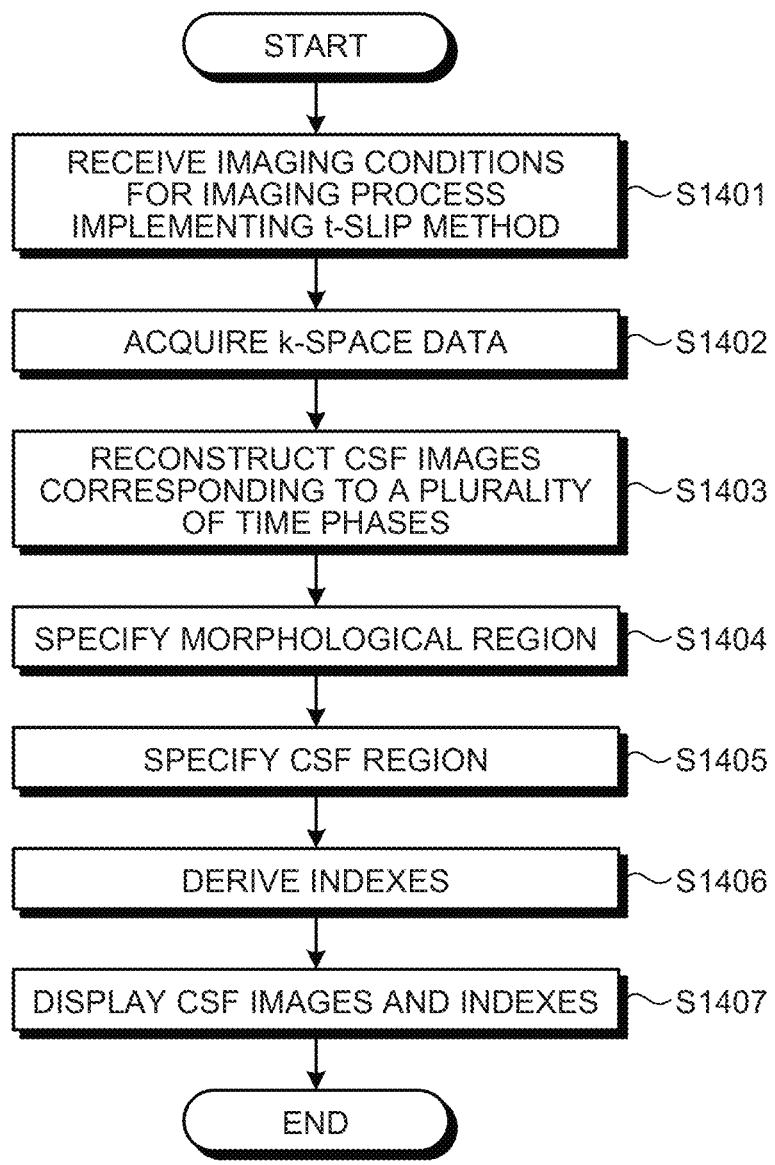

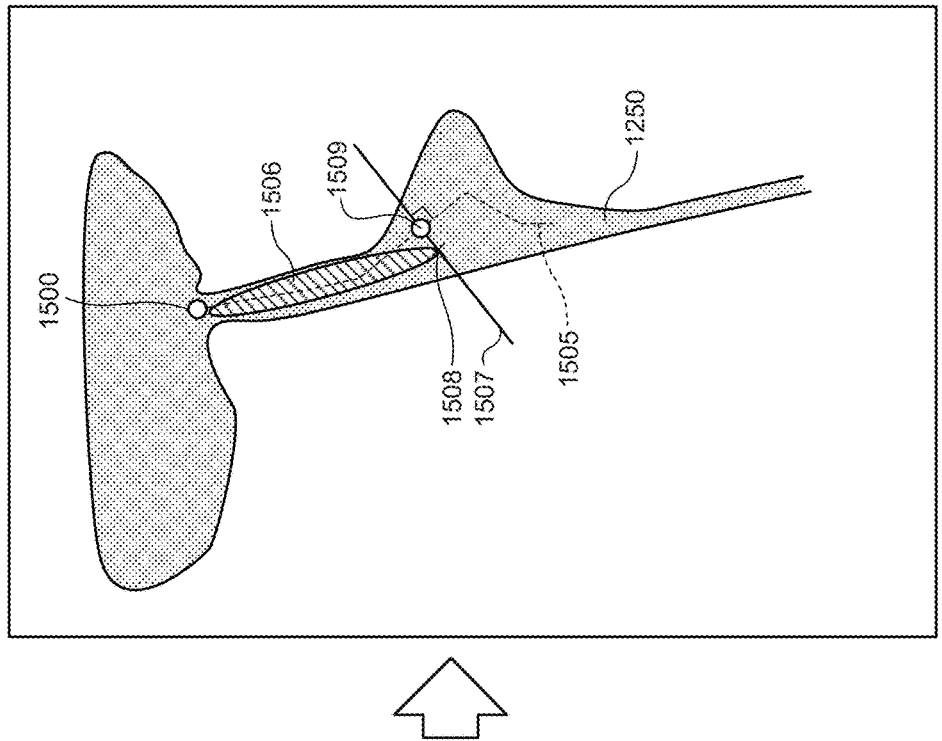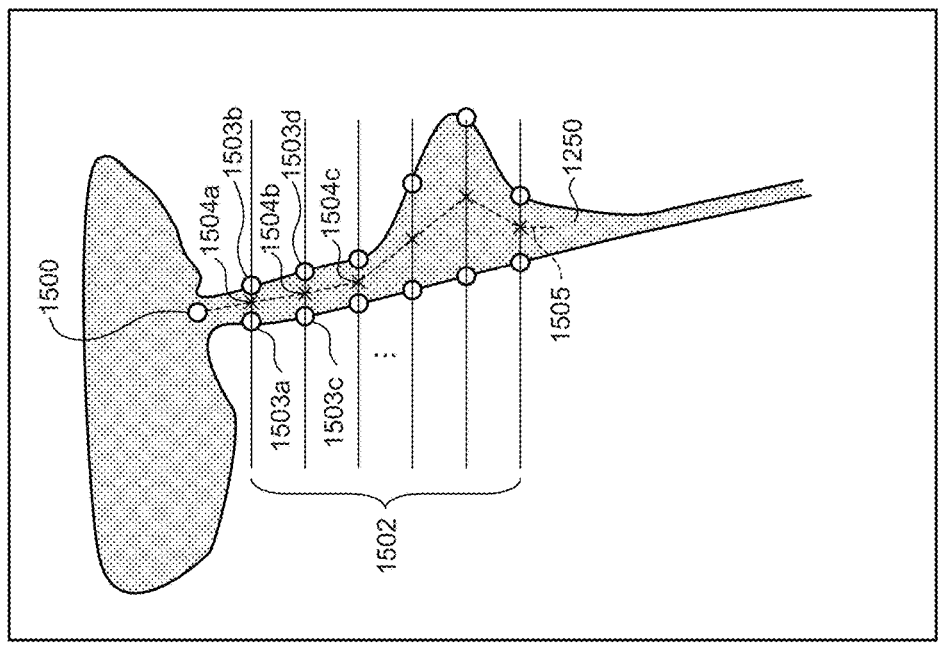
FIG.15A

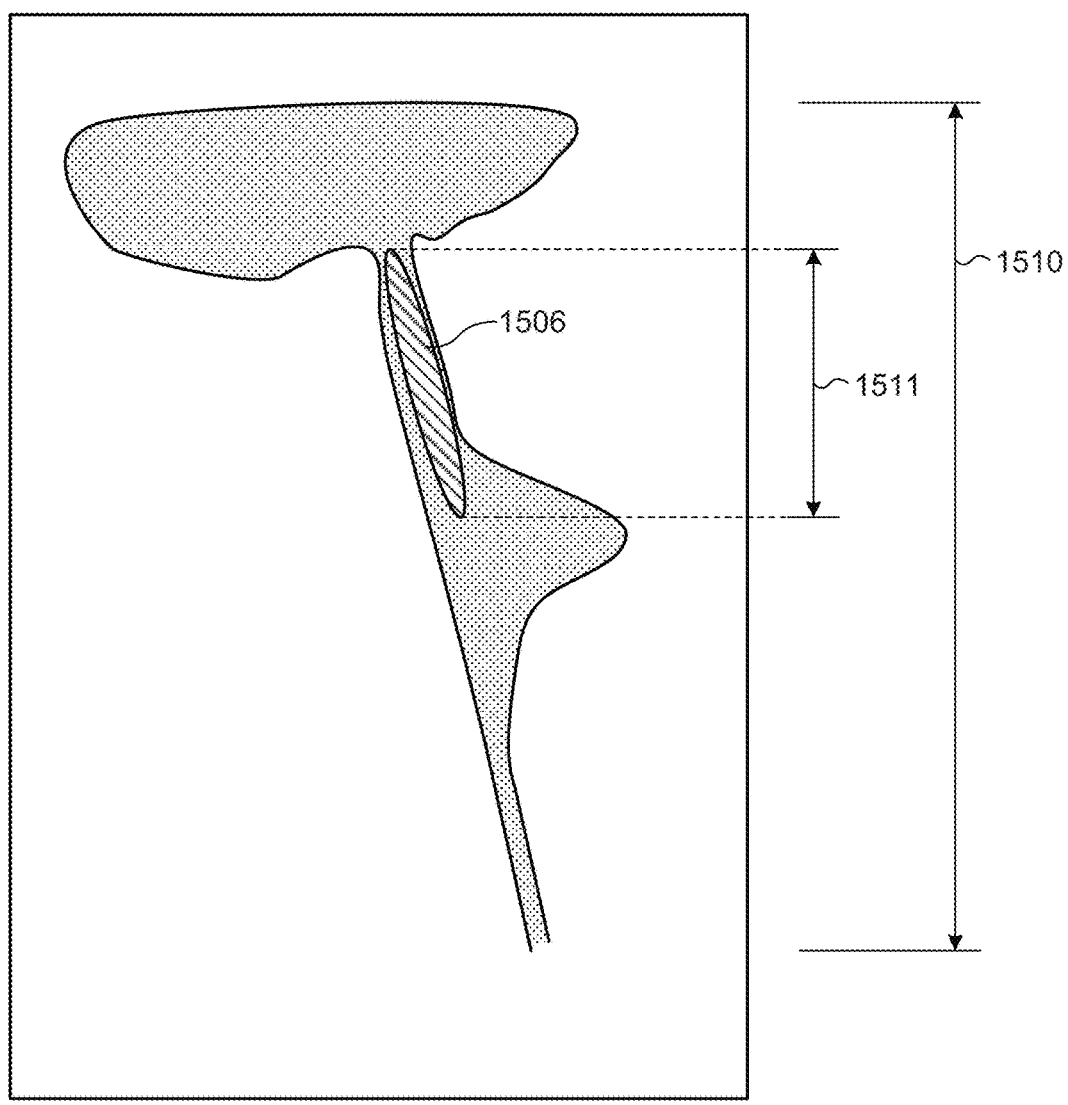

IMAGE PROCESSING OF FLOWING FLUIDS WITHIN IMAGED ATONOMICAL STRUCTURE

CROSS-REFERENCE TO RELATED APPLICATIONS

This application is based upon and claims the benefit of priority from Japanese Patent Application No. 2012-103928, filed on Apr. 27, 2012; and Japanese Patent Application No. 2013-062743, filed on Mar. 25, 2013, the entire contents of all of which are incorporated herein by reference.

FIELD

Embodiments described herein relate generally to an image processing apparatus and a magnetic resonance imaging apparatus.

BACKGROUND

Magnetic resonance imaging is an imaging (image taking) method by which a nuclear spin in an examined subject (hereinafter, a "subject") placed in a magnetostatic field is magnetically excited with a Radio Frequency (RF) pulse at a Larmor frequency so that an image is reconstructed from Nuclear Magnetic Resonance (NMR) signals generated due to the excitation.

Conventionally, in the field of magnetic resonance imaging, Magnetic Resonance Angiography (MRA) has been known as a method for obtaining an image of blood, which is a body fluid (hereinafter, a "fluid" as appropriate) flowing in subjects. Of MRA methods, methods that do not use a contrast agent are called non-contrast MRA. Among methods for performing non-contrast MRA, for example, a method called Time Spatial Labeling Inversion Pulse (Time-SLIP) method has been known by which an MR image is taken after a predetermined time period has elapsed since a labeling process is performed by applying an Inversion Recovery (IR) pulse to a fluid.

BRIEF DESCRIPTION OF THE DRAWINGS

FIG. 5 is a flowchart of a processing procedure according to the first embodiment;
FIG. 12 is a block diagram of a controlling unit according to a second embodiment;
FIG. 13 presents drawings of an example of a morphological region according to the second embodiment;
FIG. 14 is a flowchart of a processing procedure according to the second embodiment;
FIG. 15A is a drawing of an index deriving process according to the second embodiment;
FIG. 15B is another drawing of the index deriving process according to the second embodiment.

DETAILED DESCRIPTION

Figure 1:
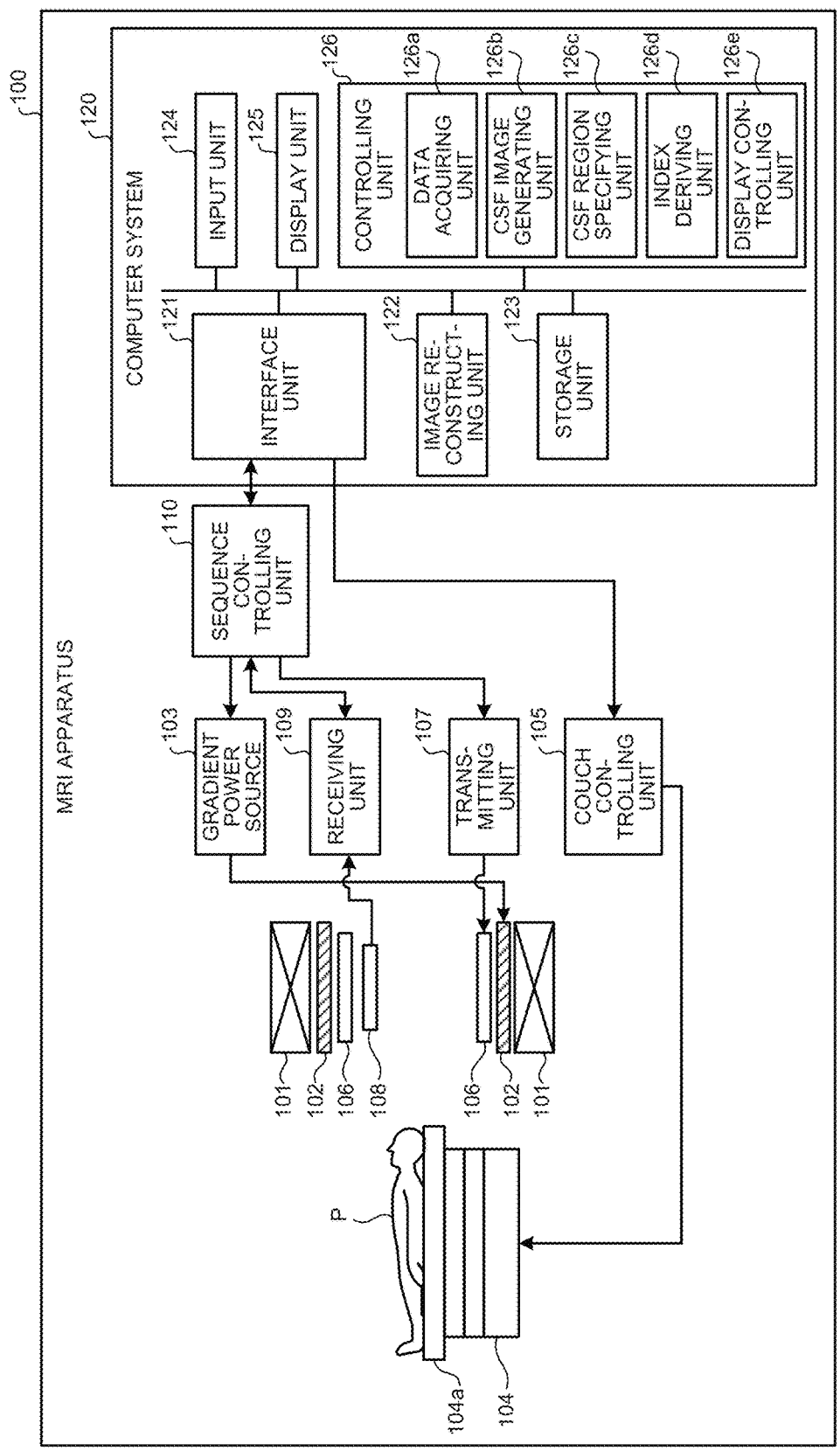
FIG. 1 is a block diagram of a Magnetic Resonance Imaging (MRI) apparatus according to a first embodiment.

An image processing apparatus according to an embodiment includes a specifying unit and a deriving unit. The specifying unit specifies a fluid region in a plurality of magnetic resonance images that are acquired by applying a labeling pulse to a label region and that are mutually related. The deriving unit derives an index indicating dynamics of a fluid on a basis of the specified fluid region.

Exemplary embodiments of an image processing apparatus and an image display apparatus, as well as magnetic resonance imaging apparatus (hereinafter, "MRI apparatus", as appropriate) and method will be explained in detail, with reference the accompanying drawings. In the exemplary embodiments described below, the elements identified with the same reference numerals are assumed to perform the same operation, and the explanation thereof will be omitted as appropriate.

First Embodiment

FIG. 1 is a block diagram of an MRI apparatus 100 according to a first embodiment. As shown in FIG. 1, the MRI apparatus 100 according to the first embodiment includes a magnetostatic field magnet 101, a gradient coil 102, a gradient power source 103, a couch 104, a couch controlling unit 105, a transmission RF coil 106, a transmitting unit 107, a reception RF coil 108, a receiving unit 109, a sequence controlling unit 110, and a computer system 120. An examined subject (hereinafter, a "subject") P is not included in the MRI apparatus 100.

The magnetostatic field magnet 101 is a magnet formed in the shape of a hollow circular cylinder and generates a uniform magnetostatic field in the space on the inside thereof. The magnetostatic field magnet 101 may be configured by using, for example, a permanent magnet or a superconductive magnet. The gradient coil 102 is a coil formed in the shape of a hollow circular cylinder and is disposed on the inside of the magnetostatic field magnet 101. The gradient coil 102 is formed by combining three coils corresponding to X-, Y-, and Z-axes that are orthogonal to one another. These three coils individually receive electric current from the gradient power source 103 and generate gradient magnetic fields of which the magnetic field intensities change along the X-, Y-, and Z-axes. It is assumed that the Z-axis direction is the same as the direction of the magnetostatic field.

The gradient power source 103 supplies electric current to the gradient coil 102. In this situation, the gradient magnetic fields on the X-, Y-, and Z-axes that are generated by the gradient coil 102 correspond to, for example, a slice-selecting-purpose gradient magnetic field Gs, a phase-encoding-purpose gradient magnetic field Ge, and a read-out-purpose gradient magnetic field Gr, respectively. The slice-selecting-purpose gradient magnetic field Gs is used for determining an imaging cross section in an arbitrary manner. The phase-encoding-purpose gradient magnetic field Ge is used for changing the phase of an NMR signal according to a spatial position. The read-out-purpose gradient magnetic field Gr is used for changing the frequency of an NMR signal according to a spatial position.

The couch 104 includes a couchtop 104a on which the subject P is placed. Under control of the couch controlling unit 105, while the subject P is placed thereon, the couchtop 104a is inserted into the hollow (i.e., an imaging opening) of the gradient coil 102. Normally, the couch 104 is provided so that the longitudinal direction thereof extends parallel to the central axis of the magnetostatic field magnet 101. Under control of the computer system 120, the couch controlling unit 105 drives the couch 104 so that the couchtop 104a moves in the longitudinal direction and in an up-and-down direction.

The transmission RF coil 106 is disposed on the inside of the gradient coil 102 and generates a radio-frequency magnetic field by receiving a supply of a Radio Frequency (RF) pulse from the transmitting unit 107. The transmitting unit 107 supplies the RF pulse corresponding to a Larmor frequency to the transmission RF coil 106.

The reception RF coil 108 is disposed on the inside of the gradient coil 102 and receives NMR signals emitted from the subject P due to an influence of the radio-frequency magnetic field. When having received the NMR signals, the reception RF coil 108 outputs the received NMR signals to the receiving unit 109.

The receiving unit 109 generates k-space data on the basis of the NMR signals being output from the reception RF coil 108. More specifically, the receiving unit 109 generates the k-space data by applying a digital conversion to the NMR signals being output from the reception RF coil 108. The k-space data is kept in correspondence with information about spatial frequencies in the Phase Encode (PE) direction, the Read Out (RO) direction, and the Slice Encode (SE) direction by the slice-selecting-purpose gradient magnetic field Gs, the phase-encoding-purpose gradient magnetic field Ge, and the read-out-purpose gradient magnetic field Gr. Further, the receiving unit 109 transmits the generated k-space data to the sequence controlling unit 110. The receiving unit 109 may be provided on a gantry device side where the magnetostatic field magnet 101, the gradient coil 102, and like are provided.

The sequence controlling unit 110 performs an imaging process on the subject P, by driving the gradient power source 103, the transmitting unit 107, and the receiving unit 109, based on sequence information transmitted from the computer system 120. In this situation, the sequence information is information that defines a procedure for performing the imaging process. The sequence information defines, for example, the intensity of the power source to be supplied by the gradient power source 103 to the gradient coil 102 and the timing with which the power source is to be supplied; the strength of the RF pulse to be transmitted by the transmitting unit 107 to the transmission RF coil 106 and the timing with which the RF pulse is to be applied; and the timing with which the NMR signals are to be detected by the receiving unit 109.

When the sequence controlling unit 110 has received the k-space data from the receiving unit 109, as a result of driving the gradient power source 103, the transmitting unit 107, and the receiving unit 109 and taking the image of the subject P, the sequence controlling unit 110 transfers the received k-space data to the computer system 120.

The computer system 120 exercises overall control of the MRI apparatus 100, acquires data, and reconstructs images, for example. The computer system 120 includes an interface unit 121, an image reconstructing unit 122, a storage unit 123, an input unit 124, a display unit 125, and a controlling unit 126.

The interface unit 121 transmits the sequence information to the sequence controlling unit 110 and receives the k-space data from the sequence controlling unit 110. When having received the k-space data, the interface unit 121 stores the received k-space data into the storage unit 123.

The image reconstructing unit 122 generates spectrum data and image data by applying a reconstructing process such as a Fourier transform process to the k-space data stored in the storage unit 123. The storage unit 123 stores therein, for example, the k-space data received by the interface unit 121 and the image data generated by the image reconstructing unit 122. For example, the storage unit 123 is configured by using a semiconductor memory element such as a Random Access Memory (RAM) or a flash memory, a hard disk, an optical disk, or the like. The input unit 124 receives various types of instructions and inputs of information from an operator. The input unit 124 is configured by using a pointing device such as a mouse or a trackball, a selecting device such as a mode changing switch, and/or an input device such as a keyboard. Under control of the controlling unit 126, the display unit 125 displays various types of information such as the spectrum data and the image data. The display unit 125 is configured by using, for example, a display device such as a liquid crystal display device.

The controlling unit 126 exercises overall control of the MRI apparatus 100. More specifically, the controlling unit 126 controls the imaging process by generating the sequence information based on imaging conditions input from the operator via the input unit 124 and transmitting the generated sequence information to the sequence controlling unit 110. Further, the controlling unit 126 controls the image reconstructing process performed based on the k-space data transmitted from the sequence controlling unit 110 as a result of the imaging process and controls the display process performed by the display unit 125. For example, the controlling unit 126 is configured by using an integrated circuit such as an Application Specific Integrated Circuit (ASIC) or a Field Programmable Gate Array (FPGA), or an electronic circuit such as a Central Processing Unit (CPU) or a Micro Processing Unit (MPU).

The MRI apparatus 100 according to the first embodiment is configured to acquire images corresponding to a plurality of time phases along a time series by applying a labeling pulse to a label region in which a fluid is flowing and to derive indexes indicating dynamics of the fluid by analyzing each of the acquired images. Also, in the first embodiment, the fluid is assumed to be cerebrospinal fluid (hereinafter, "CSF", as appropriate). The process is realized mainly by functional units included in the controlling unit 126. For example, as shown in FIG. 1, the controlling unit 126 includes a data acquiring unit 126a, a CSF image generating unit 126b, a CSF region specifying unit 126c, an index deriving unit 126d, and a display controlling unit 126e.

Figure 2:
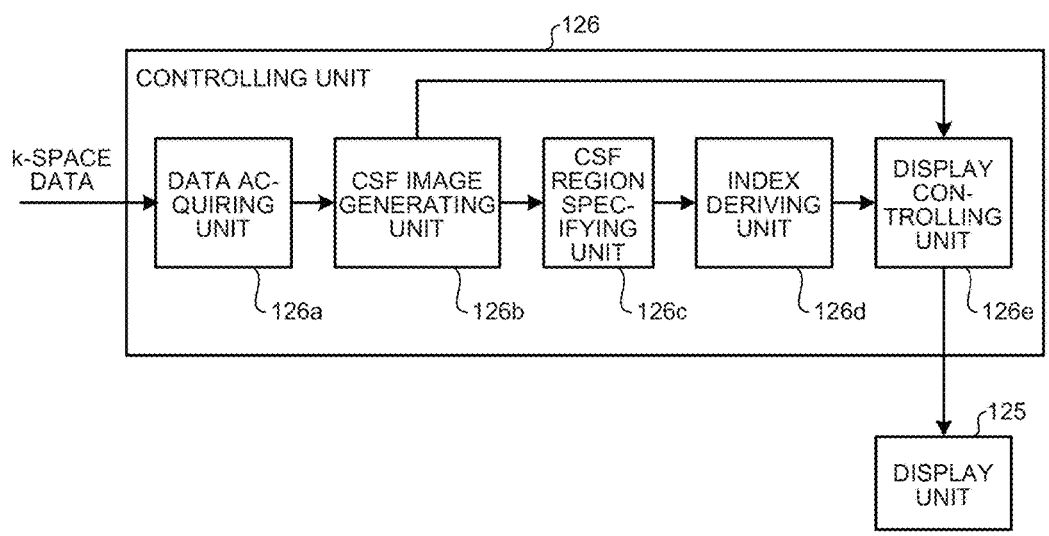
FIG. 2 is a block diagram of a controlling unit according to the first embodiment.

FIG. 2 is a block diagram of the controlling unit 126 according to the first embodiment. The data acquiring unit 126a is configured to acquire CSF images corresponding to a plurality of time phases. For example, the data acquiring unit 126a acquires k-space data corresponding to a plurality of time phases by controlling the sequence controlling unit 110 and the like and applying a labeling pulse to a label region where CSF is flowing. Further, the data acquiring unit 126a transmits the acquired k-space data to the CSF image generating unit 126b.

In this situation, for example, the data acquiring unit 126a acquires the CSF images corresponding to the plurality of time phases by implementing a Time Spatial Labeling Inversion Pulse (Time-SLIP) method (hereinafter, a "t-SLIP method", as appropriate), without using any contrast agent.

Figure 3:
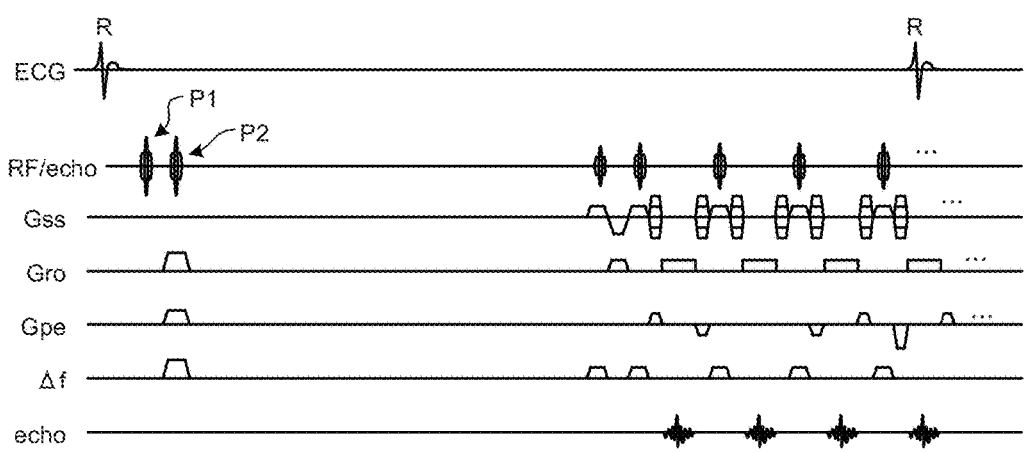
FIG. 3 is a chart of a pulse sequence according to the first embodiment.
Figure 4A:
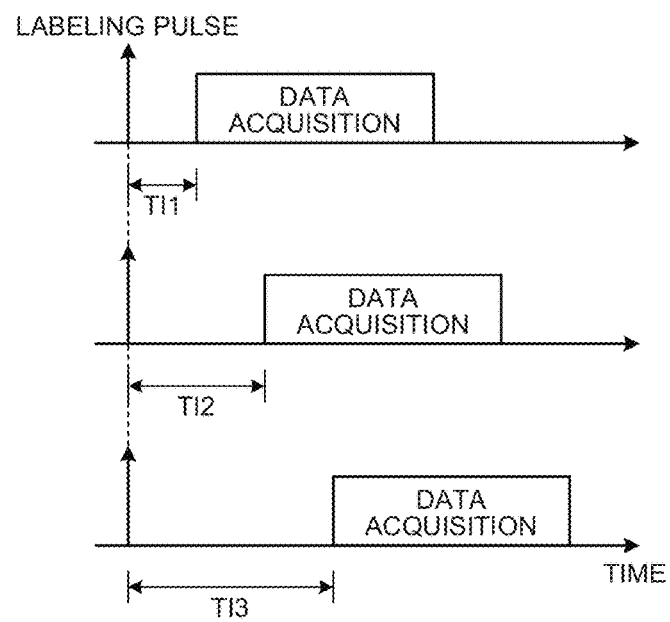
FIG. 4A is a chart of a pulse sequence according to the first embodiment.
Figure 4B:
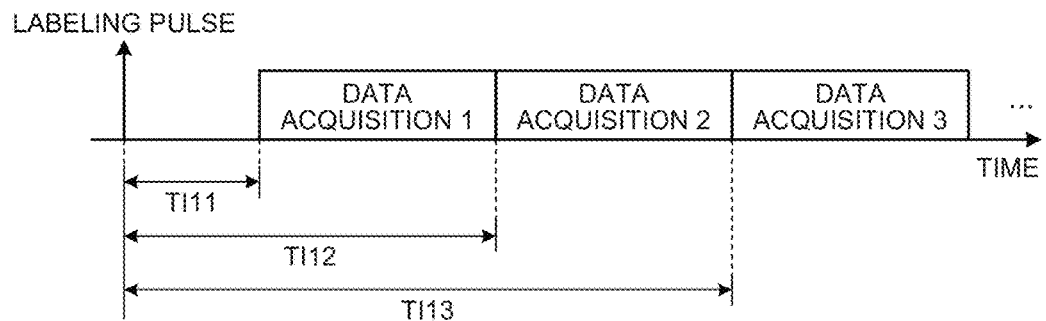
FIG. 4B is another chart of a pulse sequence according to the first embodiment.

FIGS. 3, 4A, and 4B are charts of pulse sequences according to the first embodiment. In FIGS. 3, 4A, and 4B, the horizontal axis expresses time. The t-SLIP method is a method by which a fluid flowing out to or flowing into an imaging region is labeled in a label region that is independent of the imaging region so that the fluid is selectively rendered by raising or lowering the signal value of the fluid flowing out to or flowing into the imaging region. In other words, the t-SLIP method is a method for visualizing the fluid.

As shown in FIG. 3, according to the t-SLIP method, the fluid flowing in the label region is labeled by, for example, applying an inversion recovery pulse (hereinafter, an "IR pulse", as appropriate) as the labeling pulse. Further, data ("echo") is acquired when a Traveling Time (TI) period has elapsed since the time at which the labeling pulse is applied. The TI period is appropriately configured in accordance with imaging conditions such as the position in which the label region is set, the position in which the imaging region where the fluid is to be rendered is set, and a relaxation period for a longitudinal magnetization in a background portion, and the like. Further, as shown in FIG. 3, the labeling pulse includes a non-region-selecting IR pulse P1 and a region-selecting IR pulse P2. These pulses are applied substantially at the same time. It should be noted, however, that it is possible to selectively determine whether the non-region-selecting IR pulse P1 should be applied or not. Further, it is possible to arbitrarily set the label region, which is the region where the region-selecting IR pulse P2 is applied, independently of the imaging region. It is also acceptable to configure the imaging conditions so that a plurality of labeling pulses are applied.

In this situation, examples of imaging methods implementing the t-SLIP method include a flow-in method and a flow-out method. The flow-in method is a method by which the longitudinal magnetization in an imaging region is inversed by applying a region-selecting IR pulse to the imaging region, so as to render the fluid flowing into the imaging region from the outside of the imaging region and having not been labeled. In contrast, the flow-out method is a method by which the longitudinal magnetization is inversed by applying a non-region-selecting IR pulse to an imaging region, and also, the longitudinal magnetization of the fluid in a label region is inversed to a positive value by applying a region-selecting IR pulse to the label region, so as to selectively render the fluid flowing out from the label region to the imaging region and having been labeled. For example, according to the flow-in method, the label region is set to be the imaging region, whereas according to the flow-out method, the label region is set within the imaging region. The definitions of the flow-in method and the flow-out method are not limited to those presented above. These methods may be referred to by opposite names or by other names, depending on the manner in which these methods are defined. Further, the settings of the imaging region and the label region may be arbitrarily changed according to the purpose of an imaging purpose or the like.

Thus, it is possible to determine data acquisition timing so that data acquisition is started after the fluid has flowed into the imaging region. Further, if the longitudinal magnetization of the background portion is inversed by a non-region-selecting IR pulse, it is also acceptable to determine the data acquisition timing in such a manner that the data acquisition is started at a time when the absolute value of the longitudinal magnetization in the background portion becomes close to zero due to a longitudinal relaxation.

As the sequence used for acquiring the imaging data in the example shown in FIGS. 3, 4A, and 4B, it is possible to use an arbitrary sequence such as a Steady State Free Precession (SSFP) sequence, a Fast Asymmetric Spin Echo (FASE) sequence, or a Fast Advanced Spin Echo (FASE) sequence.

Further, the labeling process to make the fluid recognizable may be performed by applying the labeling pulse to the label region or the imaging region. Examples of pulses that can be used as the labeling pulse include an IR pulse, a saturation (SAT) pulse, a Spatial Modulation of Magnetization (SPAMM) pulse, and a Delays Alternating with Nutations for Tailored Excitation (DANTE) pulse.

A region-selecting SAT pulse is a pulse that causes a longitudinal magnetization to saturate by turning a magnetization vector in a selected slab region by 90 degrees.

Further, it is also possible to configure the imaging conditions so that not only a single SAT pulse but a plurality of SAT pulses are applied. When a plurality of SAT pulses are applied, it is possible to set a plurality of selected slab regions in a radial pattern or a striped pattern.

The SPAMM pulse may also be referred to as a rest grip pulse. The SPAMM pulse was originally developed for monitoring movements of the heart. The SPAMM pulse is applied as a non-region-selecting pulse and is able to form, by adjusting the gradient magnetic field, a region saturated with a desired pattern such as a striped pattern, a grid pattern (a lattice pattern), a radial pattern, or the like. Because the saturated pattern functions as a position marker, it is possible to obtain an image rendering the flow of a body fluid, as a result of the imaging process involving the application of the SPAMM pulse.

The DANTE pulse is also a labeling pulse that is able to form a region saturated with a desired pattern such as a striped pattern, a grid pattern, a radial pattern, or the like. The SPAMM pulse and the DANTE pulse are equivalent to a plurality of SAT pulses applied at the same time.

Further, it is also possible to configure the imaging conditions in such a manner that pulses obtained by combining one or more IR pulses or SAT pulses with a SPAMM pulse or a DANTE pulse are applied as the labeling pulse.

Further, when the timing with which the labeling pulse such as the IR pulse, the SAT pulse, the SPAMM pulse, or the DANTE pulse is applied is determined on the basis of a trigger signal, examples of the trigger signal include a biological signal such as an electrocardiogram (ECG) signal, a synchronized signal from a respiratory sensor (a respiratory synchronization), or a pulse-wave synchronized signal called a Peripheral Pulse Gating (PPG) signal, or any other arbitrary signal such as a clock signal. When the ECG signal or the PPG signal is used, an ECG unit or a PPG signal detecting unit is connected to the MRI apparatus 100.

The data acquiring unit 126a according to the first embodiment is configured to acquire the data corresponding to the plurality of time phases, for the purpose of evaluating the dynamics of the CSF. Examples of the method for acquiring the data include the following two methods: In a first method, as shown in FIG. 4A, the data acquiring unit 126a applies a labeling pulse to a label region and, when a predetermined time period (the TI period) has elapsed, the data acquiring unit 126a acquires a piece of data of the image region "corresponding to one time phase". Further, as shown in FIG. 4A, while changing the TI period from "TI1" to "TI2", then to "TI3", and so on, the data acquiring unit 126a acquires a piece of data "corresponding to one time phase" every time. Thus, the data acquiring unit 126a is able to acquire the pieces of data corresponding to the plurality of time phases, i.e., the pieces of data in a plurality of frames corresponding to the different times. In this situation, setting many TI periods with small increments makes it possible to view the dynamics of the CSF corresponding to smaller temporal changes.

In a second method, as shown in FIG. 4B, after applying a labeling pulse to a label region, the data acquiring unit 126a repeatedly performs the data acquisition multiple times consecutively (e.g., a data acquisition 1, a data acquisition 2, a data acquisition 3, and so on). The pieces of data from the multiple data acquisitions that are acquired in the temporally consecutive manner have mutually-different TI periods such as "TI11", "TI12", "TI13", and so on. Thus, after applying the labeling pulse one time, the data acquiring unit 126a is able to acquire the pieces of data corresponding to the plurality of time phases, i.e., the pieces of data in a plurality of frames corresponding to the different times. In the second method also, setting many TI periods with small increments makes it possible to view the dynamics of the CSF corresponding to smaller temporal changes.

Returning to the description of FIG. 2, the CSF image generating unit 126b is configured to generate the CSF images corresponding to the plurality of time phases. For example, the CSF image generating unit 126b generates the CSF images corresponding to the plurality of time phases by controlling the image reconstructing unit 122 and the like so as to perform an image reconstructing process using the k-space data transmitted from the data acquiring unit 126a. Further, the CSF image generating unit 126b transmits the generated CSF images corresponding to the plurality of times phases to the CSF region specifying unit 126c and to the display controlling unit 126e.

The CSF region specifying unit 126c specifies a region where the CSF is present (hereinafter, a "CSF region", as appropriate) in each of the CSF images corresponding to the plurality of time phases. For example, the CSF region specifying unit 126c specifies the CSF regions by analyzing each of the CSF images corresponding to the plurality of time phases and having been transmitted from the CSF image generating unit 126b. Further, the CSF region specifying unit 126c transmits the CSF images corresponding to the plurality of time phases and CSF region information to the index deriving unit 126d. Details of the process performed by the CSF region specifying unit 126c will be explained later.

The index deriving unit 126d is configured to derive indexes indicating the dynamics of the CSF, on the basis of each of the CSF regions. For example, the index deriving unit 126d identifies predetermined feature values (e.g., the position of the CSF, the area size of the CSF region) in each of the CSF regions, by using the CSF images corresponding to the plurality of time phases and the CSF region information trans-mitted from the CSF region specifying unit 126c and derives indexes such as the position of the CSF and the area size of the CSF region) at each of predetermined times, as well as speed information of the CSF calculated as an average of the plurality of time phases, by tracing a locus of the fluctuation of each of the identified feature values in the CSF images corresponding to the plurality of time phases. Further, the index deriving unit 126d transmits the derived indexes to the display controlling unit 126e. Details of the process performed by the index deriving unit 126d will be explained later.

The display controlling unit 126e displays the indexes derived by the index deriving unit 126d on the display unit 125. For example, the display controlling unit 126e causes the position of the CSF at each of the predetermined times derived along the time series to be displayed on the display unit 125 along the time series. Details of the process performed by the display controlling unit 126e will be explained later.

Figure 6:
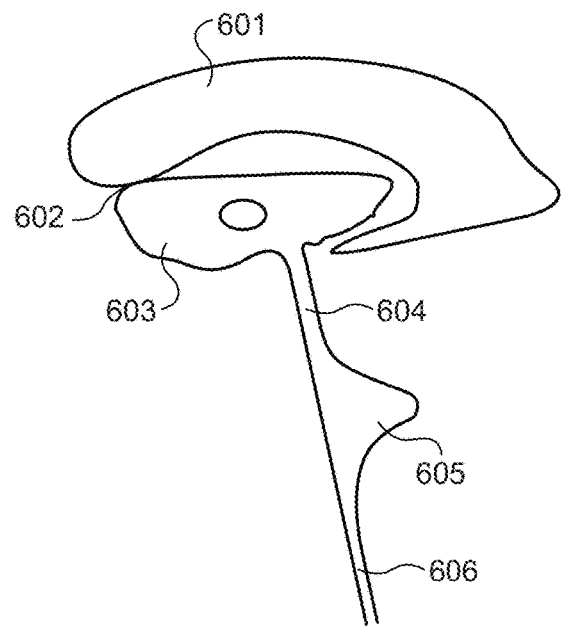
FIG. 6 is a drawing indicating anatomical positions of characteristic sites in the brain according to the first embodiment.

Next, FIG. 5 is a flowchart of a processing procedure according to the first embodiment. As mentioned above, the site serving as the processing target in the first embodiment is CSF in the brain. FIG. 6 is a drawing indicating anatomical positions of characteristic sites in the brain according to the first embodiment. FIG. 6 illustrates an image (hereinafter, a "sagittal image", as appropriate) taken on a plane (referred to as a "sagittal cross section" or a "sagittal plane") that divides the brain into a left section and a right section. The sagittal image illustrated in FIG. 6 includes the lateral ventricle 601, the foramen of Monro 602, the third ventricle 603, the cerebral aqueduct 604, the fourth ventricle 605, and the central canal 606.

As shown in FIG. 5, in the MRI apparatus 100, the controlling unit 126, at first, receives imaging conditions for an imaging process performed by implementing the t-SLIP method, from the operator via the input unit 124 (step S501).

Figure 7:
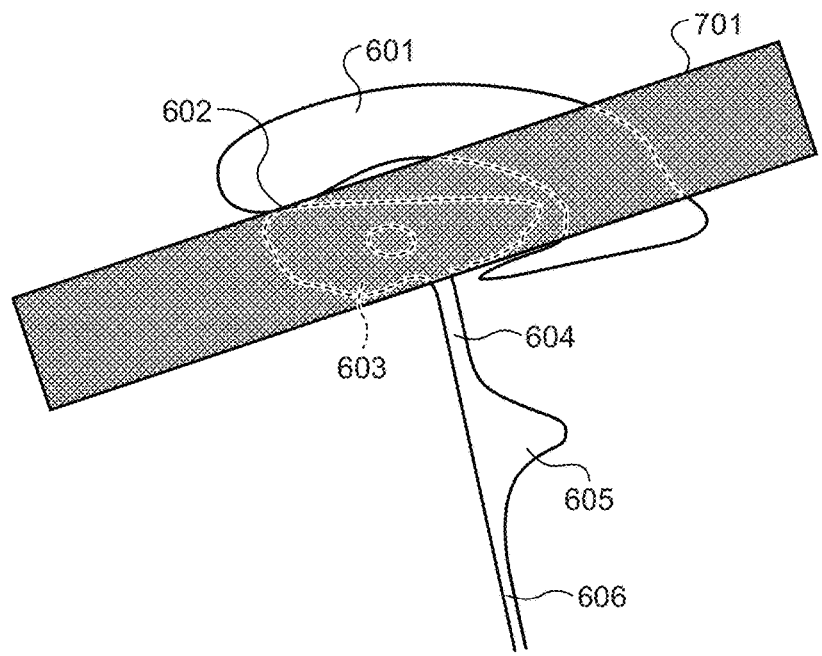
FIG. 7 is a drawing of an imaging region and a label region according to the first embodiment.

FIG. 7 is a drawing of an imaging region and a label region according to the first embodiment. As shown in FIG. 7, in the first embodiment, the imaging region is set so as to make it possible to view the CSF along a moving direction and/or a diffusion direction of the CSF. In the sagittal image illustrated in FIG. 7, it is possible to view, typically, the CSF flowing out from the third ventricle 603 to the cerebral aqueduct 604 and from the cerebral aqueduct 604 to the fourth ventricle 605, for example. Further, in the first embodiment, a label region 701 is set within the imaging region. For example, as shown in FIG. 7, the label region 701 is set in the third ventricle 603, which is positioned at a starting point from which the CSF flows out within the imaging region. Further, the imaging region does not necessarily have to be set so as to include all of the lateral ventricle 601, the foramen of Monro 602, the third ventricle 603, the cerebral aqueduct 604, the fourth ventricle 605, and the central canal 606. For example, it is acceptable to set an imaging region so as to include only the lateral ventricle 601 or the cerebral aqueduct 604. As mentioned above, it is sufficient if the imaging region is set so as to make it possible to view the CSF along the moving direction and/or the diffusion direction of the CSF. Thus, depending on the purpose of the imaging process or the like, it is possible to arbitrarily change which characteristic site of the brain should be included in the setting of an imaging region. In some situations, it may be possible to view the manner in which CSF flows into the label region 701 from the outside of the label region 701.

Returning to the description of FIG. 5, when the operator has instructed to start the imaging process, the data acquiring unit 126a acquires k-space data based on NMR signals, by generating sequence information of a pulse sequence according to the t-SLIP method and transmitting the generated sequence information to the sequence controlling unit 110 (step S502). Further, by applying a reconstructing process such as a discrete two-dimensional Fourier transform process to the k-space data acquired at step S501, the CSF image generating unit 126b generates a CSF image sequence made up of CSF images corresponding to a plurality of time phases (step S503).

Figure 8:
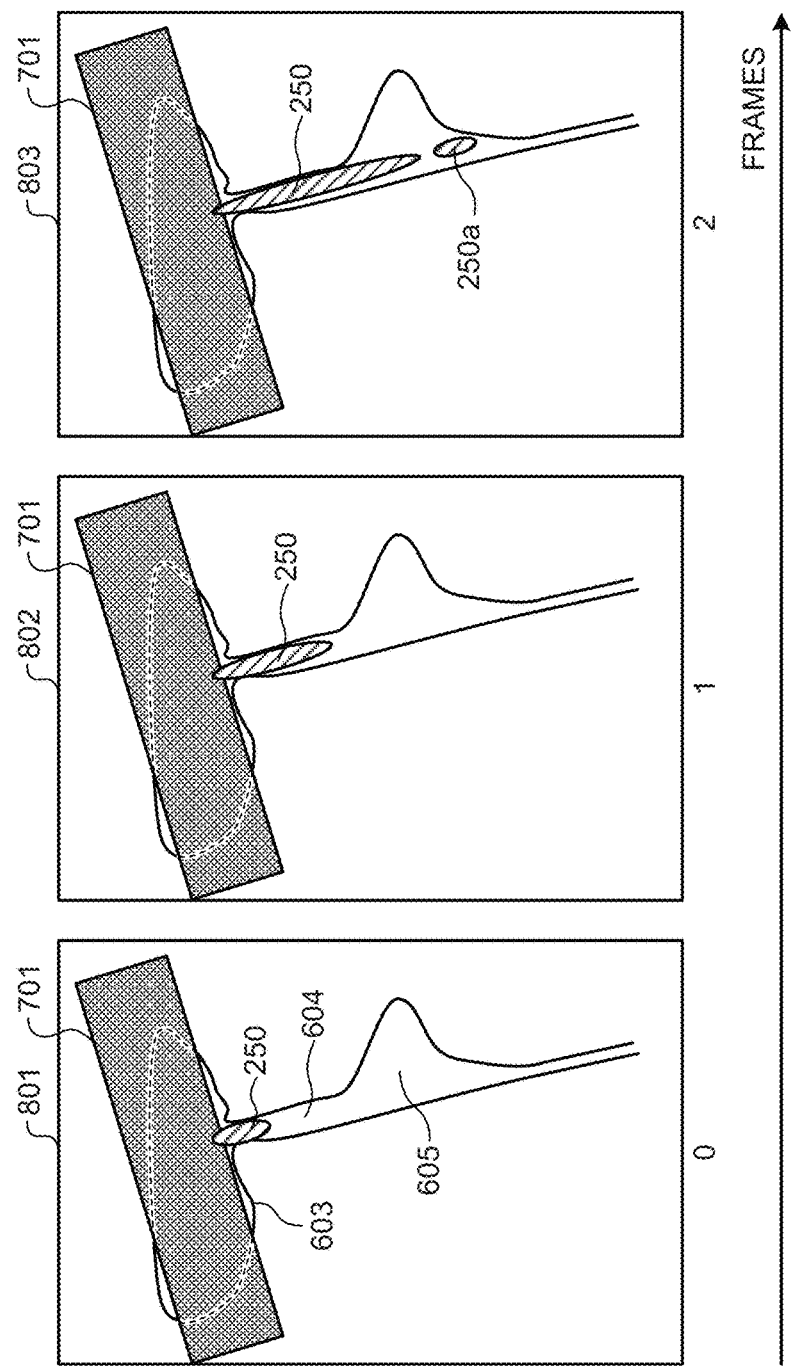
FIG. 8 is an example of a cerebrospinal fluid (CSF) image sequence according to the first embodiment.

FIG. 8 is a drawing of an example of a CSF image sequence according to the first embodiment. In FIG. 8, frames 801, 802, 803, and so on represent a CSF image sequence made up of a series of images that were obtained by reconstructing k-space data resulting from data acquisitions with mutually-different TI periods as illustrated in FIGS. 4A and 4B. As shown in FIG. 8, the CSF image sequence is arranged according to the times, the imaging timing, or the frame numbers. Further, from the CSF image sequence illustrated in FIG. 8, it is possible to view the manner in which a CSF region 250 and a CSF region 250a that were labeled in the label region 701 are flowing from the third ventricle 603 to the cerebral aqueduct 604 and from the cerebral aqueduct 604 to the fourth ventricle 605.

Returning to the description of FIG. 5, the CSF region specifying unit 126c subsequently specifies a CSF region in each of the CSF images corresponding to the plurality of time phases and having been generated at step S503 (step S504).

For example, the CSF region specifying unit 126c specifies a CSF region 250 in each of the CSF images by performing an analysis while using a k-means clustering method or a discriminant analysis method. For example, during the analysis, the CSF region specifying unit 126c uses the difference in image signal intensities between the CSF region 250 that flowed out after having been labeled and other regions. Examples of the other regions include regions that have not been labeled such as the cerebral aqueduct 604, the fourth ventricle 605, and the like, as well as the parenchymal region of the brain, which is not shown in the drawings.

In another example, the CSF region specifying unit 126c may specify the CSF region 250 as a result of the operator's manually specifying a region via the input unit 124. For example, the CSF region specifying unit 126c may display the CSF image sequence generated by the CSF image generating unit 126b on the display unit 125 and may receive a specification of the CSF region 250 as a result of the operator's manual operation performed on each of the images in the CSF image sequence.

In yet another example, the CSF region specifying unit 126c may specify the CSF region 250 by performing an analysis using a clustering process based on a transition, a variance, or an average value of the image signal intensities over the course of time. Because the transition of the image signal intensity over the course of time varies depending on whether a region is a label region or not and whether CSF is present therein or not. Thus, it is effective to utilize the characteristics of the image signal intensity transition. In yet another example, the CSF region specifying unit 126c may specify the CSF region 250 by performing an analysis using an Active Counter Model (ACM) or an Active Shape Model (ASM). In that situation, for example, the CSF region specifying unit 126c uses shape information indicating that the CSF region 250 is substantially rectangular. In yet another example, the CSF region specifying unit 126c may specify the CSF region 250 by performing an analysis while using knowledge about biological structures through which CSF is speculated to pass. In that situation, for example, the CSF region specifying unit 126c uses knowledge about biological structures indicating that the fourth ventricle 605 is positioned below the third ventricle 603 and that the cerebral aqueduct 604 connects these two ventricles together. In yet another example, the CSF region specifying unit 126c may specify the CSF region 250 by performing a three-dimensional (3D) analysis while using other cross-sectional images or cross-sectional images acquired through a multi-slice imaging process. Further, the CSF region specifying unit 126c may specify the CSF region 250 by combining together two or more of the methods described above.

Further, the index deriving unit 126d derives indexes indicating dynamics of the CSF, on the basis of each of the CSF regions 250 specified at step S504 (step S505).

Figure 9A:
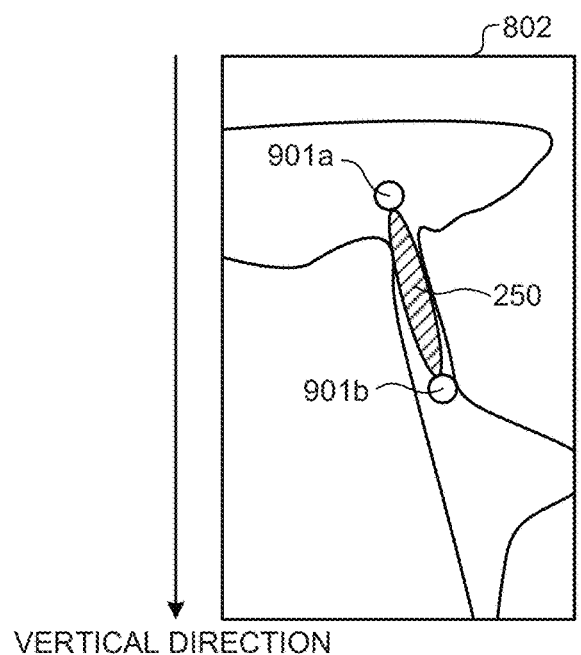
FIG. 9A is a drawing of an index deriving process according to the first embodiment.
Figure 9B:
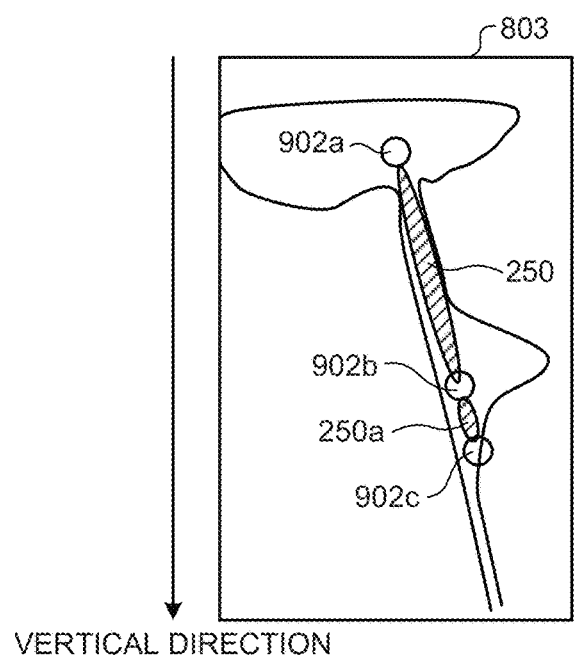
FIG. 9B is another drawing of the index deriving process according to the first embodiment.

FIGS. 9A and 9B are drawings of an index deriving process according to the first embodiment. FIG. 9A is an enlarged view of a part of the frame 802 illustrated in FIG. 8. First, within the CSF region 250 in the frame 802, the index deriving unit 126d determines the position being the smallest in the horizontal direction and the vertical direction to be a reference position 901a and subsequently specifies such a position (i.e., a position 901b) within the CSF region 250 that has the longest distance from the reference position 901a to be a CSF position. In other words, in this situation, the CSF position used as an index of dynamics of the CSF is the distance from the opposite end of the CSF region.

Alternatively, to calculate the distance from the reference position 901a, the index deriving unit 126d may use any arbitrary distance scale such as a city block distance or a Euclidean distance. It is also acceptable to use a directional component projected onto an arbitrary straight line (e.g., a straight line along the cerebral aqueduct). Further, the CSF position does not necessarily have to be the position of the pixel having the longest distance from the reference position; it is acceptable to use, for example, the position of the pixel at a gravity point within the CSF region.

Further, FIG. 9B is an enlarged view of a part of the frame 803 illustrated in FIG. 8. In the frame 803, the CSF region is represented as separate regions indicated as the CSF region 250 and the CSF region 250a. In that situation, for example, within the CSF region 250 that is connected to the reference position 902a, the index deriving unit 126d specifies such a position within the CSF region 250 that has the longest distance from the reference position 902a as a position of the CSF serving as a feature value (hereinafter, a "CSF position", as appropriate). In this situation, a position 902b in FIG. 9B is specified as the CSF position. In another example, within the CSF region 250a, which is not connected to the reference position 902a, the index deriving unit 126d may specify such a position within the CSF region 250a that has the longest distance from the reference position 902a, as the CSF position. In this situation, a position 902c in FIG. 9B is specified as the CSF position. In the latter situation, for example, the index deriving unit 126d may judge whether the CSF region 250 and the CSF region 250a are in a predetermined connected relationship while using a threshold value and may specify a position within the CSF region 250a as the CSF position if a condition is satisfied where the two regions are judged to be in the predetermined connected relationship.

Further, in the first embodiment, the index deriving unit 126d further derives velocity information calculated as an average of a plurality of frames, as another index indicating dynamics of the CSF. For example, the index deriving unit 126d calculates a regression line that is expressed by Expression (1) shown below and that is obtained when the frames (corresponding to the times) are plotted on the X-axis and the CSF positions are plotted on the Y-axis. The index deriving unit 126d may calculate the regression line using all the frames or a part of the frames.

$$Y = aX + b \quad (1)$$

In Expression (1), X denotes a frame number (a time), whereas Y denotes the distance of the CSF position corresponding to the time X, while "a" denotes the slope of the regression line, and "b" denotes an offset. Because "a" denotes a moving amount of the CSF position per frame, it is possible to calculate a CSF moving amount per unit time period, i.e., the velocity calculated as an average of the plurality of frames, by converting the frames into times while using the time periods between the frames (a frame rate).

Further, the index deriving unit 126d may use area sizes of the CSF region as an index indicating dynamics of the CSF. The index deriving unit 126d calculates the area size of the CSF region for each of the frames, in units of the number of pixels or square meters. Similar to the example with the CSF position, by calculating the slope "a" of the regression line while using the frame number (the time) as X and the area size of the CSF region as Y in Expression (1), it is possible to calculate the velocity of the expansion and the diffusion of the CSF region per unit time period, i.e., the velocity of the expansion or the diffusion of the CSF region calculated as an average of the plurality of frames.

In another example, besides the slope "a" of the regression line expressed in Expression (1), the index deriving unit 126d may use any of the following statistical values (a) to (f) below as an index indicating dynamics of the CSF. In particular, the total variation norms in unit time periods shown under (a) are useful because the values correspond to the velocity calculated as an average of the plurality frames, like the slope "a" of the regression line in Expression (1).

(a) Total variation norms of the CSF position corresponding to the acquisition times of the CSF images or an average value of the total variation norms;

(b) A time-direction variance of the CSF position corresponding to the acquisition times of the CSF images (c) The slope of a regression line indicating a relationship between the area sizes of the CSF region and the corresponding acquisition times of the CSF images;

(d) Total variation norms of the area sizes of the CSF region corresponding to the acquisition times of the CSF images or an average value of the total variation norms;

(e) A time-direction variance of the area sizes of the CSF region corresponding to the acquisition times of the CSF images; and (f) Moving amounts of the CSF position corresponding to the acquisition times of the plurality of CSF images and a unit moving amount normalized with the acquisition times.

Returning to the description of FIG. 5, the display controlling unit 126e subsequently displays, on the display unit 125, the indexes derived by the index deriving unit 126d at step S505 (step S506).

Figure 10A:
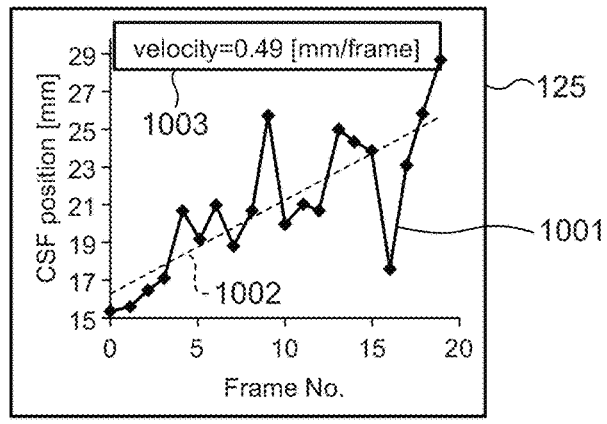
FIG. 10A is an exemplary display according to the first embodiment.
Figure 10B:
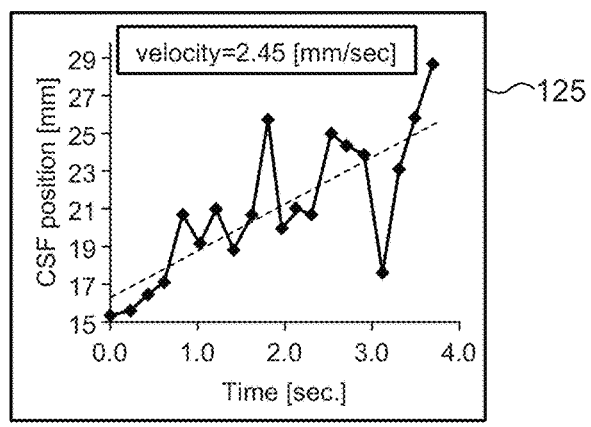
FIG. 10B is another exemplary display according to the first embodiment.
Figure 10C:
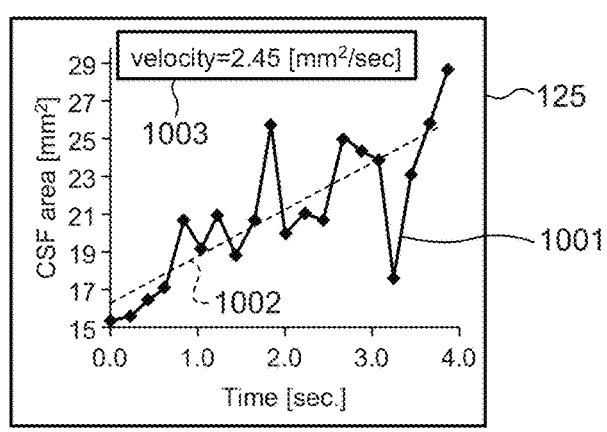
FIG. 10C is yet another exemplary display according to the first embodiment.

FIGS. 10A to 10C are exemplary displays according to the first embodiment. The display controlling unit 126e according to the first embodiment exercises control so that the indexes derived by the index deriving unit 126d are displayed on the display unit 125. For example, as shown in FIGS. 10A to 10C, the display controlling unit 126e displays, on the display unit 125, plot lines 1001 each of which indicates, for each of the predetermined times, the position of the CSF and the amount of change in the area size of the CSF region that shift over the course of time.

For example, in FIG. 10A, the X-axis expresses frame numbers ("Frame No."), whereas the Y-axis expresses the position of the CSF ("CSF position"). The display controlling unit 126e plots the position of the CSF in each of the frames (the black diamonds in FIG. 10A) and displays a regression line 1002 expressed by Expression (1) above and velocity information 1003 corresponding to the slope "a" of the regression line. The viewer who views the display is able to easily understand the position of the CSF in each of the frames and the velocity information calculated as an average of the plurality of frames and is therefore able to appropriately evaluate the dynamics of the CSF in each of the frames as well as the dynamics of the CSF calculated as an average of the plurality of frames. In other words, the CSF position is, as explained above, such a position in the CSF region that has the longest distance from the reference position, for example. In the example in FIG. 10A, together with the specific numerical value information, dynamics are displayed with regard to the CSF that does not necessarily keep moving in one direction, but moves forward and backward in a direction away from the reference position and in a direction toward the reference position, and that gradually moves, as a whole, in a direction away from the reference position over the course of time.

In another example, as shown in FIG. 10B, it is acceptable to configure a chart so that the X-axis expresses time, starting with a point in time at which the first frame was acquired. Alternatively, for example, the X-axis may express an elapsed time period as a TI period (e.g., the time period from the application of an IR pulse to the application of an excitation pulse). In yet another example, the Y-axis may express the area size of the CSF region, as shown in FIG. 10C. In this example, the display controlling unit 126e plots the area size of the CSF region at each of the predetermined times (the black diamonds in FIG. 10C) and displays the regression line 1002 expressed by Expression (1) above and velocity information 1003 corresponding to the slope "a" of the regression line. The viewer who views the display is able to easily understand the area size of the CSF region at each of the times and the diffusion velocity information of the CSF region calculated as an average of the plurality of frames and is therefore able to appropriately evaluate the dynamics of the CSF in each of the frames as well as the dynamics of the CSF calculated as an average of the plurality of frames. In other words, in the example in FIG. 10C, together with the specific numerical value information, dynamics are displayed with regard to the CSF that does not necessarily keep diffusing, but repeatedly diffuses and contracts and that, as a whole, gradually diffuses over the course of time.

The method for displaying the dynamics of the CSF at each of the predetermined times and the dynamics of the CSF calculated as an average of the plurality of frames is not limited to the example described above. For example, it is sufficient if the display controlling unit 126e displays at least one selected from the plot line 1001, the regression line 1002, and the velocity information 1003. Further, it is also possible to select or combine, as appropriate, what is expressed by the X-axis and by the Y-axis.

Figure 11:
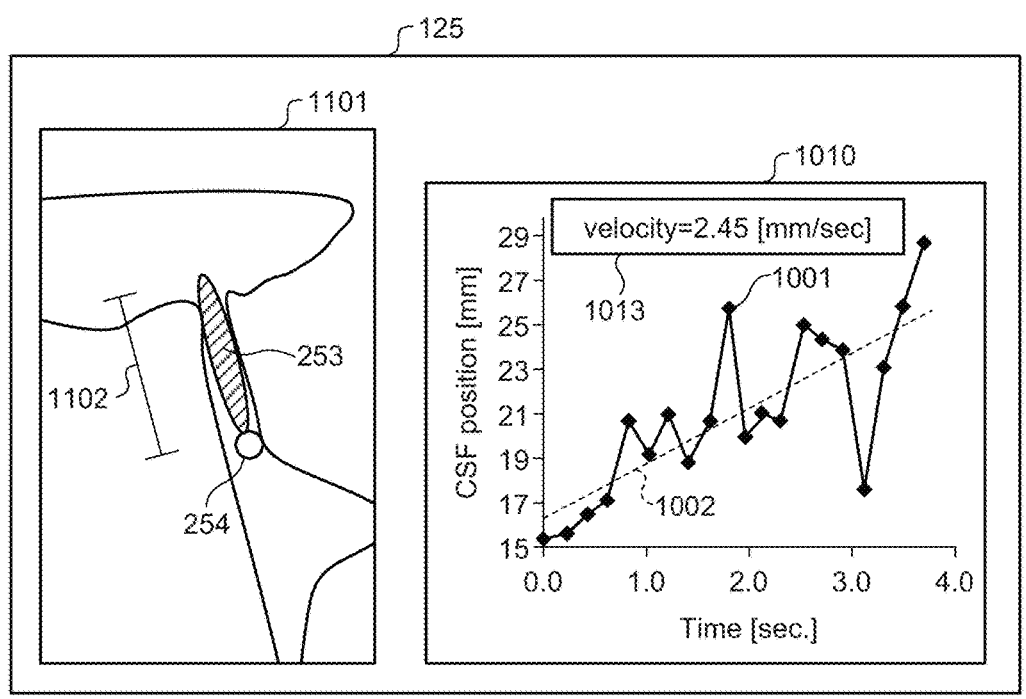
FIG. 11 is yet another exemplary display according to the first embodiment.

FIG. 11 is yet another exemplary display according to the first embodiment. The display controlling unit 126e according to the first embodiment may be configured to display the indexes derived by the index deriving unit 126d, and to further display, on the display unit 125, at least one of the CSF images corresponding to the plurality of time phases generated by the CSF image generating unit 126b, in such a manner that the CSF position and the CSF region are displayed while being superimposed on the CSF image. For example, as shown in FIG. 11, the display controlling unit 126e displays, on the display unit 125, a superimposed image 1101 realized by displaying a CSF position 254 and a CSF region 253 in a superimposed manner, as well as a plot chart 1010, which are arranged side by side. Further, for example, as shown in FIG. 11, the display controlling unit 126e displays a bar 1102 so as to visualize the distance from the reference position to the CSF position 254.

In this situation, for example, the display controlling unit 126e may display the superimposed images 1101 in the plurality of time phases corresponding to the CSF images in the plurality of time phases, as a moving picture configured with predetermined time intervals. For example, the display controlling unit 126e may display the superimposed images 1101 as a moving picture by updating the plot line 1001 in the plot chart 1010 in synchronization with the timing with which the superimposed images 1101 are switched from one to another. For example, it is acceptable to configure the plot chart 1010 in such a manner that the number of plots gradually increases over the course of time. Further, when displaying the superimposed images 1101 as a moving picture, the display controlling unit 126e may display the entire plot line 1001 of the plot chart 1010 from the beginning.

In yet another example, the display controlling unit 126e may select a CSF image corresponding to one time phase from among the CSF images corresponding to the plurality of time phases and may display the superimposed image 1101 corresponding to the CSF image in the selected time phase as a still picture. For example, the display controlling unit 126e may select a frame in the first time phase or a frame in the last time phase from among the CSF images corresponding to the plurality of time phases and may display the CSF image of the selected frame as a still picture. For example, if the frame in the first time phase has been selected, a display is realized so that the label region 701 that has just been labeled can be viewed in the superimposed image 1101. Thus, the viewer is able to recognize the relationship between the label region 701 and the CSF. In contrast, if the frame in the last time phase has been selected, for example, because the longitudinal magnetization of the label region 701 is restored, it is hardly possible to view the label region 701 in the superimposed image 1101. Thus, the viewer is able to view a CSF image in which the label region 701 is not displayed, which may be preferable as a diagnosis image, for example. In yet another example, the display controlling unit 126e may display other CSF images that are taken separately.

In yet another example, when displaying the superimposed image 1101 as a still picture, the display controlling unit 126e may display the CSF position 254 corresponding to each of the frames or may display a locus of the CSF position 254 specified in the frames, in the superimposed image 1101. In yet another example, the display controlling unit 126e may further display one or more CSF images themselves in which neither the CSF position 254 nor the CSF region 253 is superimposed, as a moving picture or as a still picture. In yet another example, the display controlling unit 126e does not necessarily have to simultaneously display the superimposed image 1101 and the plot chart 1010 arranged side by side. The display controlling unit 126e may display only one or the other. In yet another example, the display controlling unit 126e may switch between the displays of the one or more superimposed images 1101, the one or more CSF images, and the plot chart 1010.

In yet another example, the display controlling unit 126e may change display modes of the CSF region 253 and the CSF position 254. For example, let us assume that the CSF image itself in which neither the CSF position 254 or the CSF region 253 is superimposed is a grayscale image, while the RGB values in all the pixel positions are "gray". In that situation, to display the CSF region 253 in "red", the display controlling unit 126e defines the RGB values in the pixel positions corresponding to the CSF region 253 by using Expression (2) below. In Expression (2), "Rmax" denotes a maximum value (typically "255") of the R value indicating "red", whereas "rate" denotes a transmission rate of a color component with respect to a grayscale image sequence.

$$\left. \begin{array}{l} R = \text{gray}*(1.0 - \text{rate}) + R\text{max}*\text{rate} \\ G = \text{gray} \\ B = \text{gray} \end{array} \right\} \quad (2)$$

Further, to display the CSF position 254 in "green", the display controlling unit 126e defines the RGB values in the pixel position corresponding to the CSF position 254 by using Expression (3) below. In Expression (3), "Gmax" denotes a maximum value (typically "255") of the G value indicating "green".

$$\left.\begin{array}{l} R = \text{gray} \\ G = \text{gray} * (1.0 - \text{rate}) + G\text{max} * \text{rate} \\ B = \text{gray} \end{array}\right\} \quad (3)$$

As a result, because the CSF region 253 is displayed in "red" and the CSF position 254 is displayed in "green" in the superimposed image 1101, while the luminance values change in accordance with the signal intensities in the pixel positions. Thus, the operator is able to easily understand the change of the CSF position 254 in each of the frames. In the explanation above, the example is explained in which the display controlling unit 126e displays the CSF region 253 in "red" and displays the CSF position 254 in "green"; however, the display controlling unit 126e may realize the display using other colors or may realize the display using a grayscale instead of colors. Further, the bar 1102 may be colored in accordance with the distance.

As explained above, according to the first embodiment, the CSF region specifying unit 126c specifies the CSF region in each of the plurality of images obtained by implementing the t-SLIP method by which the images are reconstructed by detecting the signals of the fluid flowing out from the labeled region. Further, the index deriving unit 126d derives the indexes indicating the dynamics of the CSF by using the CSF positions and the area sizes of the CSF region. After that, the display controlling unit 126e displays the derived indexes on the display unit 125. Consequently, according to the first embodiment, it is possible to obtain the changes of the fluid and the velocity information that are observed locally between the frames or per unit time period. In other words, it is possible to appropriately evaluate the dynamics of the fluid in the body of the subject.

Which is to say, clinically speaking, if the fluid has stopped moving, it is possible to determine, with certainty, that the fluid has stopped moving. Further, it is also possible to visualize how the fluid moves. For example, when the fluid is CSF, hydrocephalus is known to exhibit changes in the velocity of CSF, i.e., the CSF moves faster in some sites and moves slower in other sites. Thus, the MRI apparatus 100 according to the first embodiment is able to aid processes of distinguishing hydrocephalus symptoms from non-hydrocephalus symptoms.

Fluids such as CSF have no periodicity unlike cardiac cycles. Thus, the flow of a fluid significantly varies for each data acquisition time. Purposes of observing dynamics of fluids may vary. For example, in some situations, it may be necessary to precisely examine whether a fluid is circulating or whether there is traffic of fluids into a cavity that is apparently closed. In those situations, it is important to find out velocity values such as the maximum flow rate and an average flow rate, as well as to find out how far a fluid in a certain location can travel within a certain time period. In this regard, according to the first embodiment, it is possible to appropriately evaluate the dynamics of a fluid, even if, as mentioned above, the fluid has no periodicity in terms of changes in the flow rate thereof.

Second Embodiment

Next, a second embodiment will be explained. The second embodiment is different from the first embodiment in that a morphological region corresponding to anatomical morphology where CSF is flowing is specified at first within an imaging region, before a CSF region is specified. The MRI apparatus 100 according to the second embodiment has almost the same configuration as that of the MRI apparatus 100 according to the first embodiment, except for the technical features particularly mentioned below. Thus, the explanation thereof will be omitted as appropriate.

FIG. 12 is a block diagram of the controlling unit 126 according to the second embodiment. As shown in FIG. 12, the controlling unit 126 according to the second embodiment further includes a morphological region specifying unit 126f. Accordingly, the index deriving unit 126d also derives indexes by using methods different from those in the first embodiment.

The morphological region specifying unit 126f is configured to specify a morphological region corresponding to anatomical morphology where CSF is flowing, within an imaging region. For example, the morphological region specifying unit 126f specifies the morphological region by analyzing each of the CSF images corresponding to the plurality of time phases and having been transmitted from the CSF image generating unit 126b. Further, the morphological region specifying unit 126f transmits the CSF images corresponding to the plurality of time phases and morphological region information to the CSF region specifying unit 126c. For example, the morphological region is, typically, a region where CSF is present such as a cerebral aqueduct region, a third ventricle region and a fourth ventricle region, or a pontocerebellar cistern region.

FIG. 13 presents drawings of an example of a morphological region according to the second embodiment. FIG. 13 illustrates sagittal images of the brain. In the second embodiment, by using the same method as the one used in the specifying process performed by the CSF region specifying unit 126c, the morphological region specifying unit 126f first specifies a large region 1301 that is larger than a morphological region within an imaging region, before specifying a morphological region 1250 within the specified large region 1301. The method used by the CSF region specifying unit 126c and the method used by the morphological region specifying unit 126f can be different from each other.

For example, the morphological region specifying unit 126f may specify the large region 1301 as a result of the operator's manually specifying a region via the input unit 124. For example, the morphological region specifying unit 126f may display the CSF image sequence generated by the CSF image generating unit 126b on the display unit 125 and may receive a specification of the large region 1301 as a result of the operator's manual operation performed on each of the images in the CSF image sequence. In another example, the morphological region specifying unit 126f may specify the large region 1301 within an imaging region 1300 by performing an analysis while using a k-means clustering method or a discriminant analysis method. In yet another example, the morphological region specifying unit 126f may specify the large region 1301 by performing an analysis using a clustering process based on a transition, a variance, or an average value of the image signal intensities over the course of time. In yet another example, the morphological region specifying unit 126f may specify the large region 1301 by performing an analysis using an ACM or an ASM. In yet another example, the morphological region specifying unit 126f may specify the large region 1301 by performing an analysis while using knowledge about biological structures. In yet another example, the morphological region specifying unit 126f may specify the large region 1301 by performing a 3D analysis while using other cross-sectional images or cross-sectional images acquired through a multi-slice imaging process. Further, the morphological region specifying unit 126f may specify the large region 1301 by combining together two or more of the methods described above.

The morphological region specifying unit 126f does not necessarily have to specify the large region 1301 in each of all the frames; the morphological region specifying unit 126f may specify the large region 1301 only in one or more of the frames. Further, the morphological region specifying unit 126f may specify the entire area of a frame (the entire area of the imaging region 1300) as a large region 1301. In other words, the morphological region specifying unit 126f may omit the process of specifying the large region 1301.

Subsequently, the morphological region specifying unit 126f specifies the morphological region 1250 within the specified large region 1301. For example, the morphological region specifying unit 126f may specify the morphological region 1250 as a result of the operator's manually specifying a region via the input unit 124. For example, the morphological region specifying unit 126f may display the CSF image sequence generated by the CSF image generating unit 126b on the display unit 125 and may receive a specification of the morphological region 1250 as a result of the operator's manual operation performed on each of the images in the CSF image sequence. In another example, the morphological region specifying unit 126f may specify the morphological region 1250 within the large region 1301 by performing an analysis while using a k-means clustering method or a discriminant analysis method. In yet another example, the morphological region specifying unit 126f may specify the morphological region 1250 by performing an analysis using a clustering process based on a transition, a variance, or an average value of the image signal intensities over the course of time. In yet another example, the morphological region specifying unit 126f may specify the morphological region 1250 by performing an analysis using an ACM or an ASM. In yet another example, the morphological region specifying unit 126f may specify the morphological region 1250 by performing an analysis while using knowledge about biological structures. In yet another example, the morphological region specifying unit 126f may specify the morphological region 1250 by performing a 3D analysis while using other cross-sectional images or cross-sectional images acquired through a multi-slice imaging process. Further, the morphological region specifying unit 126f may specify the morphological region 1250 by combining together two or more of the methods described above.

Although the large region 1303 illustrated in FIG. 13 includes a label region 1305 that has been labeled, it is acceptable to configure the morphological region specifying unit 126f so as to specify a region excluding the label region 1305, as a morphological region 1250. Further, although the example was explained in which the morphological region specifying unit 126f specifies the large region 1301 and the morphological region 1250 by using the CSF images acquired after the labeling pulse is applied, possible embodiments are not limited to this example. For example, the morphological region specifying unit 126f may specify a large region 1301 and a morphological region 1250 by using a sagittal image acquired as a positioning-determining-purpose image and may conveniently apply the result of the specifying process to the CSF images acquired after the labeling pulse is applied. In that situation, it is desirable to perform a position alignment between the position-determining-purpose image and the CSF images.

When specifying the CSF region by analyzing each of the CSF images corresponding to the plurality of time phases and having been transmitted from the morphological region specifying unit 126f, the CSF region specifying unit 126c narrows the analyzed area down to the morphological region, so as to specify the CSF region within the morphological region.

Similar to the first embodiment, the index deriving unit 126d derives indexes indicating dynamics of the CSF on the basis of each of the CSF regions. However, unlike in the first embodiment, the index deriving unit 126d derives the indexes by using a straight line or a curve that passes through the morphological region.

Next, FIG. 14 is a flowchart of a processing procedure according to the second embodiment. In the following sections, the processing procedure will be explained while mainly focusing on the parts that are different from the processing procedure according to the first embodiment explained with reference to FIG. 5. More specifically, because the processes at steps S1401 through S1403 in FIG. 14 are the same as those at steps S501 through S503 in FIG. 5, explanation thereof will be omitted.

As shown in FIG. 14, subsequent to the process at step S1403, the morphological region specifying unit 126f specifies a morphological region 1250 within the imaging region 1300 (step S1404).

The process performed by the morphological region specifying unit 126f does not necessarily have to be applied to each of all the frames. It is acceptable to apply the process to only one or more of the frames and to apply the result to the other frames by copying or the like. For example, the morphological region specifying unit 126f may specify the morphological region 1250 by applying the morphological region specifying process only to the frame corresponding to the last time phase and may copy the position of the morphological region 1250 specified by using the frame corresponding to the last time phase, onto the other frames. In this situation, it is possible to apply the processes at the subsequent stages, without the need to apply the process performed by the morphological region specifying unit 126f to each of all the frames. In another example, it is also acceptable to generate one synthesized image by applying a Maximum/Minimum Intensity Projection (MIP) process or a filtering process to a plurality of frames in mutually the same pixel positions and in a time direction and to apply the process performed by the morphological region specifying unit 126f to the generated synthesized image.

After that, the CSF region specifying unit 126c specifies a CSF region within the morphological region 1250 (step S1405). The CSF region specifying process performed by the CSF region specifying unit 126c is the same as that in the first embodiment, except that the CSF region is specified within the morphological region 1250. Thus, explanation thereof will be omitted.

Further, on the basis of each of the CSF regions specified at step S1405, the index deriving unit 126d derives indexes indicating dynamics of the CSF (step S1406). In the second embodiment, because the morphological region 1250 has been specified, for example, the index deriving unit 126d may derive the distance to the CSF position by using an upper end of the morphological region 1250 as a reference position. In other words, in this situation, the CSF position that is used as an index indicating dynamics of the CSF is the distance from the upper end of the morphological region 1250.

In the first embodiment, the index deriving unit 126d calculates the distance from the reference position 901a by using a distance scale such as a city block distance or a Euclidean distance; however, possible embodiments are not limited to this example. The index deriving unit 126d according to the second embodiment uses the morphological region 1250 to obtain a reference line used for calculating the distance and calculates the distance along the reference line.

FIGS. 15A and 15B are drawings of an index deriving process according to the second embodiment. FIG. 15A is an example of a method for calculating the distance according to the second embodiment. FIG. 15A illustrates an exemplary imaging process where an image is taken on a sagittal plane of the brain. A reference line 1505 is set so as to pass through the center of the morphological region 1250. For example, the index deriving unit 126*d* first arranges straight lines 1502 passing through the morphological region 1250 so as to be positioned at regular intervals. Typically, the straight lines 1502 are horizontal lines or vertical lines; however, as long as the straight lines 1502 are parallel to one another, the straight lines 1502 may be at any angle. FIG. 15A illustrates an example where the straight lines 1502 are horizontal lines. Subsequently, the index deriving unit 126*d* obtains pairs of intersections 1503 (e.g., 1503*a* and 1503*b*) at each of which a straight line 1502 intersects the morphological region 1250. After that, the index deriving unit 126*d* calculates a middle point 1504 (e.g., 1504*a*, 1504*b*, and so on) for each of the pairs of intersections 1503. Lastly, the index deriving unit 126*d* sets the reference line 1505 by connecting together the middle points 1504 of the pairs by using straight lines. If there are three or more middle points 1504, the index deriving unit 126*d* may set the reference line 1505 by using an arbitrary point-interpolation method such as a spline curve. The method for obtaining the reference line is not limited to the example described above. It is acceptable to configure the index deriving unit 126*d* so as to obtain the reference line by using any other technique.

Subsequently, the index deriving unit 126*d* draws a perpendicular line 1507 from a pixel position 1508 within a CSF region 1506 to the reference line 1505, so as to obtain an intersection 1509 between the reference line 1505 and the perpendicular line 1507. After that, the index deriving unit 126*d* derives a distance along the reference line 1505 by calculating the distance between a reference point 1500 and the intersection 1509 on the reference line 1505. Further, from among the pixel positions 1508 within the CSF region 1506, the index deriving unit 126*d* specifies such a pixel position that has the longest distance as a CSF position.

Alternatively, the index deriving unit 126*d* may derive a ratio of the length of the CSF region 1506 to the length of the morphological region 1250, as an index. For example, as shown in FIG. 15B, the index deriving unit 126*d* calculates a ratio of the length 1511 of the CSF region 1506 from an upper end to a lower end, to the length 1510 of the morphological region 1250 from an upper end to a lower end, which is used as a reference, by using Expression (4) shown below. It is possible to obtain an index indicating the amounts of change in the CSF position ratio by replacing the "CSF position" in the first embodiment with the "CSF position ratio". Thus, explanation thereof will be omitted.

"CSF position ratio" [%]="length of the CSF region"/"length of the morphological region" (4)

Alternatively, the index deriving unit 126*d* may specify the area size of the CSF region, instead of specifying the CSF position in each of the frames. In that situation, the index deriving unit 126*d* calculates an area ratio of the CSF region by using Expression (5) shown below. It is possible to obtain an index indicating the amounts of change in the CSF area ratio by replacing the "CSF area size" in the first embodiment with the "CSF area ratio". Thus, explanation thereof will be omitted.

"CSF region area ratio" [%]="area size of the CSF region"/"area size of the morphological region" (5)

After that, the display controlling unit 126*e* displays, on the display unit 125, the indexes derived by the index deriving unit 126*d* at step S1406 (step S1407). The operation performed by the display controlling unit 126*e* is similar to the operation performed by the display controlling unit 126*e* according to the first embodiment. It is possible to view the changes in the morphological region 1250 and the CSF at the same time, by displaying, in addition to the CSF region 250, the morphological region 1250 in a specific color so as to be superimposed on the CSF image sequence.

As explained above, in the second embodiment, the CSF region specifying unit 126*c* first specifies the region of interest in each of the plurality of images obtained by implementing the t-SLIP method by which the images are reconstructed by detecting the signals of the fluid flowing out from the labeled region. After that, the CSF region specifying unit 126*c* specifies the CSF region within the region of interest. Further, the index deriving unit 126*d* derives the indexes indicating the dynamics of the CSF by using the CSF positions and the area sizes of the CSF region. After that, the display controlling unit 126*e* displays the derived indexes on the display unit 125. Consequently, according to the second embodiment, it is possible to obtain, like in the first embodiment, the changes of the fluid and the velocity information that are observed locally between the frames or per unit time period. In other words, it is possible to appropriately evaluate the dynamics of the fluid in the body of the subject. In addition, according to the second embodiment, because the CSF region is specified after the region of interest is specified, it is possible to perform the processes efficiently.

Other Embodiments

Possible embodiments are not limited to the first and the second embodiments described above.
<Regarding the a Cross-Sectional Image>

In the first and the second embodiments described above, the example is explained in which the MRI apparatus 100 takes the sagittal images (e.g., the image illustrated in FIG. 6) while using the sagittal plane of the brain of the subject as the cross-sectional image. However, possible embodiments are not limited to this example. The MRI apparatus 100 may take images of an arbitrary region on an arbitrary cross-sectional image, so as to apply the configurations and the processes described above thereto.

Figure 16:
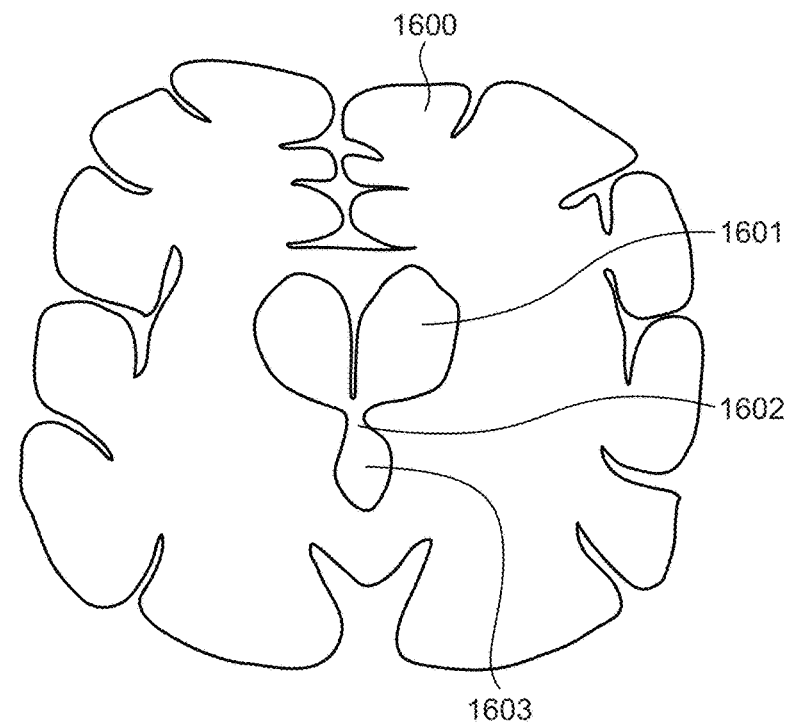
FIG. 16 is a drawing of a cross-sectional image according to another embodiment.

FIG. 16 is a drawing of a cross-sectional image according to another embodiment. FIG. 16 illustrates a plane (referred to as a "coronal cross section" or a "coronal plane") that is parallel to both the forehead and the body axis of the subject. The coronal plane illustrated in FIG. 16 indicates anatomical positions of characteristics sites of the brain where CSF is present, in addition to the parenchyma 1600 of the brain, and includes the lateral ventricle 1601, the foreman of Monro 1602, and the third ventricle 1603.

Figure 17:
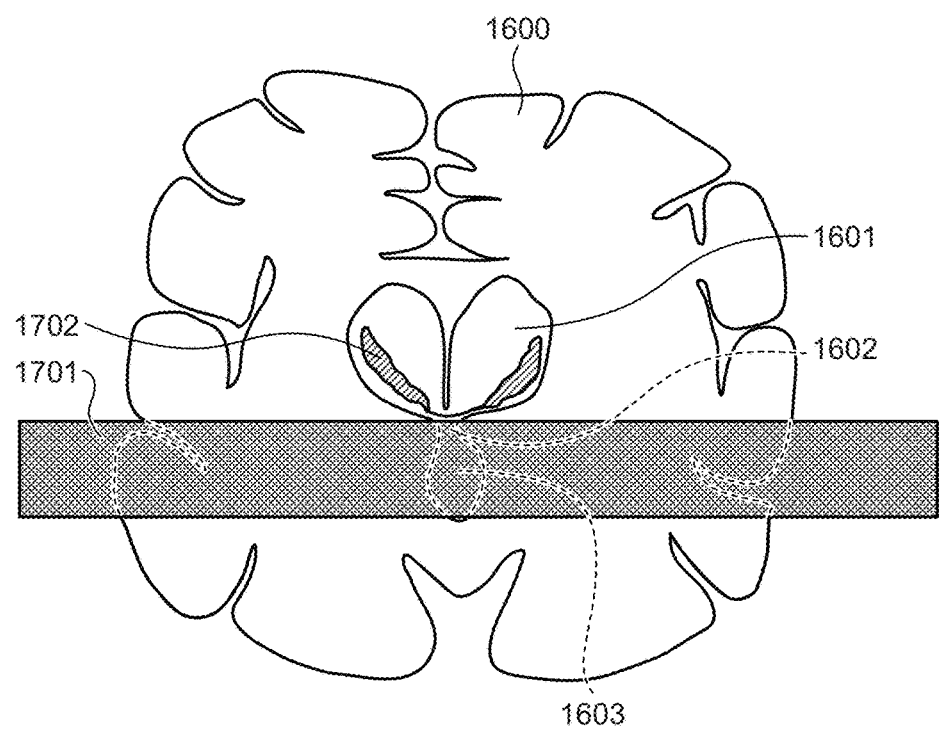
FIG. 17 is a drawing of a CSF image according to said another embodiment.

FIG. 17 is a drawing of a CSF image according to said another embodiment. The coronal image shown in FIG. 17 is a CSF image acquired by performing an imaging process implementing the t-SLIP method after setting the coronal plane shown in FIG. 16 as an imaging region and setting a label region 1701 within the imaging region. As shown in FIG. 17, it is possible to view, in the CSF image, a CSF region 1702 flowing out from the third ventricle 1603 to the lateral ventricle 1601. Consequently, in the same manner as with the sagittal images, the MRI apparatus 100 is able to specify the CSF region 1702 in the CSF images and is able to calculate indexes indicating dynamics of the CSF by specifying the CSF positions and the area sizes of the CSF region on the basis of the specified CSF region. In other words, it is sufficient if the MRI apparatus 100 sets a cross-sectional image so as to make it possible to view the CSF along the direction of the moving or the diffusion of the CSF.

As another example, it is acceptable to configure the MRI apparatus 100 so as to take images on a cross section (referred to as a "body axis cross section" or an "axial plane") that is perpendicular to a sagittal plane, a coronal plane, or the body axis of the subject, while using the spine or the cervical vertebra as a target. In this situation also, it is sufficient if the MRI apparatus 100 sets a cross-sectional image so as to make it possible to view the CSF along the direction of the moving or the diffusion of the CSF. In other words, the MRI apparatus 100 does not necessarily have to set a cross-sectional image so as to include all of the lateral ventricle 1601, the foreman of Monro 1602, and the third ventricle 1603. For example, it is acceptable to set a cross-sectional image so as to include only the lateral ventricle 1601. For example, when taking images of the spine, the MRI apparatus 100 may set an appropriate cross-sectional image and an appropriate imaging region that make it possible to view the CSF along the direction of the moving or the diffusion of the CSF.

<Regarding the Reference Position>

In the first and the second embodiments described above, the CSF position is derived as an index indicating the dynamics of the CSF. In the first and the second embodiments, the CSF position is the distance calculated by using the upper end of the CSF region or the morphological region as the reference position. However, examples of the reference position are not limited to those described in the exemplary embodiments. For example, if it is possible to obtain position information of the label region, it is acceptable for the index deriving unit 126d to use a predetermined position in the label region as the reference position. Because the position information of the label region is information that is set at the stage of planning an imaging process, the index deriving unit 126d is able to obtain the position information from, for example, the storage unit 123 storing therein the imaging conditions.

Figure 18A:
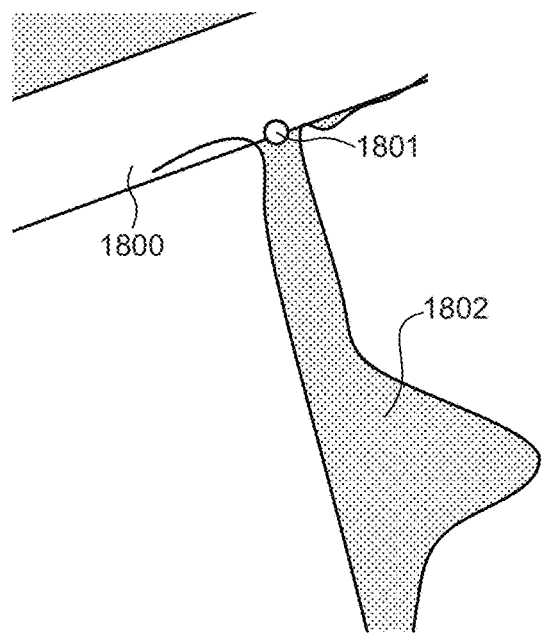
FIG. 18A is a drawing of a reference position according to yet another embodiment.
Figure 18B:
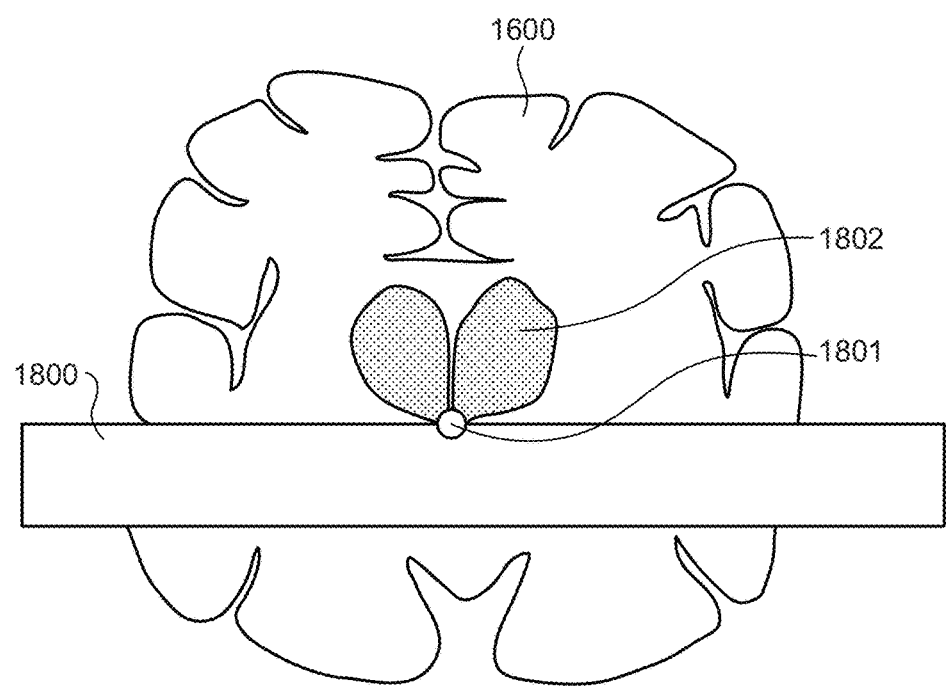
FIG. 18B is a drawing of another reference position according to said another embodiment.

FIGS. 18A and 18B are drawings of a reference position according to yet another embodiment. FIG. 18A illustrates a reference position in an image taken on a sagittal plane, whereas FIG. 18B illustrates a reference position in an image taken on a coronal plane. In FIGS. 18A and 18B, the images are enlarged as appropriate (in particular, FIG. 18A).

In FIG. 18A, a label region 1800 is set on the upper side of a morphological region 1802. In this situation, generally speaking, fluid such as CSF tends to flow out from a label region to a morphological region or to flow into a label region from a morphological region. Thus, as shown in FIG. 18A, for example, it is desirable if the index deriving unit 126d determines a boundary position between the label region 1800 and the morphological region 1802 to be a reference position 1801. In another example shown in FIG. 18B, a label region 1800 is set on the lower side of a morphological region 1802. Thus, as shown in FIG. 18B, for example, it is desirable if the index deriving unit 126d determines a boundary position between the label region 1800 and the morphological region 1802 to be a reference position 1801. For example, if the upper end of a CSF region is used as the reference position like in the first embodiment, the upper end itself serving as the reference position may also move due to the moving of the entire CSF region. In contrast, when the boundary position between the label region 1800 and the morphological region 1802 is used as the reference position, it is possible to calculate the distance more accurately. As a result, the accuracy of the index also improves. In this situation, for example, it is preferable to select, as the reference position, a pixel positioned at the center or a pixel positioned at a gravity point from among the pixels positioned on the boundary line between the label region and the morphological region. Further, in the second embodiment, the method for calculating the distance is explained with reference to FIGS. 15A and 15B. This calculation method is similarly applicable to the situation where the boundary position between the label region and the morphological region is used as the reference position.

<Regarding Specifying the CSF Region and the Morphological Region>

In the first and the second embodiments described above, the CSF region and the morphological region are specified by performing the various types of analyses or the like on the CSF images. However, possible embodiments are not limited to this example. For example, if it is possible to obtain position information of the label region, it is acceptable for the CSF region specifying unit 126c to utilize the position information for the purpose of specifying a CSF region or a morphological region. Because the position information of the label region is information that is set at the stage of planning an imaging process, the CSF region specifying unit 126c is able to obtain the position information from, for example, the storage unit 123 storing therein the imaging conditions.

It is safe to say that the imaging region is a region that includes a labeled region and a non-labeled region (e.g., a CSF region, a morphological region, and other regions). In this situation, for example, because the longitudinal magnetization of the label region, as a whole, is inversed (or saturated) by the application of a labeling pulse, the signal intensities in the label region are assumed to have values within a certain range, although there may be some differences depending on the tissue. For this reason, for example, the CSF region specifying unit 126c may calculate, in advance, an average signal intensity in the label region within the CSF image, by using the position information of the label region. Further, the CSF region specifying unit 126c is then able to specify such pixels in the non-labeled region that have values within a threshold range around the average signal intensity, as a CSF region that has flowed out from the label region to the non-labeled region. In this situation, the "threshold range" may be set in consideration of, for example, the restoration of the longitudinal magnetization.

In another example, while utilizing the fact that, not only in the label region, but the signal intensities are different from one another in a CSF region, a morphological region, and other regions included in the non-labeled region, the CSF region specifying unit 126c may specify these regions by applying a segmentation method (e.g., a k-means clustering method or a discriminant analysis method) based on the signal intensities.

<Regarding the Indexes of the Fluid Flowing Out to the Upper Side or to the Lower Side of a Label Region>

In the first and the second embodiments described above, the example is explained in which the fluid flows out in one direction with respect to the label region. However, possible embodiments are not limited to this example. It is possible to derive indexes indicating dynamics of the fluid, even in the situation where the fluid flows out in multiple directions with respect to the label region.

Figure 19A:
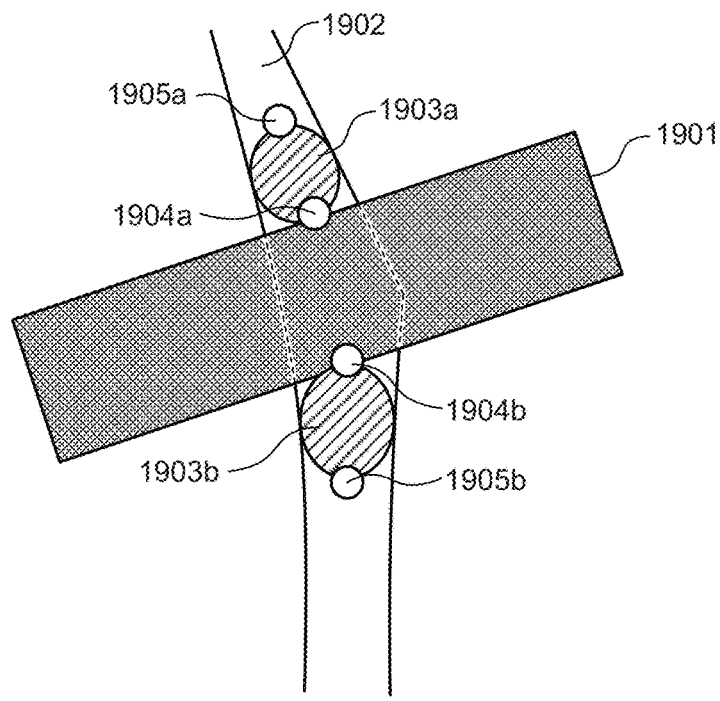
FIG. 19A is a drawing of an index deriving process according to yet another embodiment.

FIG. 19A is a drawing of an index deriving process according to yet another embodiment. FIG. 19A illustrates a CSF image acquired while using a sagittal plane of the brain as an imaging region. In the CSF image, a label region 1901 is set substantially at the center of a pontocerebellar cistern region 1902. A CSF region 1903a and a CSF region 1903b are flowing out in an upward direction and a downward direction from the label region 1901. In that situation, as shown in FIG. 19A, for example, the index deriving unit 126d determines boundary positions between a label region 1901 and a morphological region 1902 to be reference positions 1904a and 1904b. Further, the index deriving unit 126d may specify, as a CSF position, such a position (i.e., a position 1905a) within the CSF region 1903a positioned upward from the label region 1901 that has the longest distance from the reference position 1904a. Also, the index deriving unit 126d may specify, as another CSF position, such a position (i.e., a position 1905b) within the CSF region 1903b positioned downward from the label region 1901 that has the longest distance from the reference position 1904b. After that, the index deriving unit 126d may calculate a regression lines from each of the two CSF positions and may calculate velocity information calculated as an average of the plurality of frames, on the basis of the slope of the regression line for each of the two upward and downward directions from the label region 1901. In this situation, it is acceptable to use the slope of one of the regression lines as the velocity information calculated as an average of the plurality of frames. Alternatively, it is acceptable to use the maximum value of the two pieces of velocity information or an average value of the two pieces of velocity information as the velocity information calculated as an average of the plurality of frames.

Figure 19B:
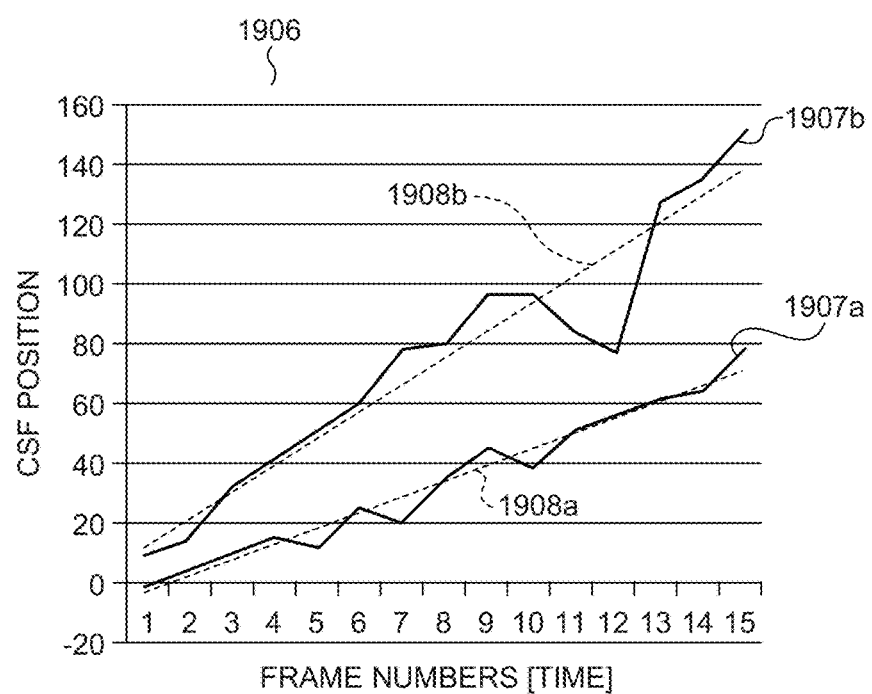
FIG. 19B is a drawing of an exemplary display according to said another embodiment.

FIG. 19B is a drawing of an exemplary display according to said another embodiment. For example, as shown in FIG. 19B, in a plot chart 1906, the display controlling unit 126e displays a plot line 1907a of the CSF position that is positioned downward from the label region 1901 and also displays a plot line 1907b of the CSF position that is positioned upward from the label region 1901. Also, as shown in FIG. 19B, for example, the display controlling unit 126e displays regression lines 1908a and 1908b, respectively. In addition, for example, the display controlling unit 126e may further display velocity information calculated on the basis of the slopes of the regression lines. In other words, it is sufficient if the display controlling unit 126e displays at least one selected from the plot chart, the regression lines, and the velocity information. Further, it is also possible to select or combine, as appropriate, what is expressed by the X-axis and by the Y-axis.

<Regarding Image Processing Such as Noise Elimination>

In the first and the second embodiments described above, it is acceptable to apply any of image processing processes including, for example, a noise elimination process (e.g., a Gaussian filter), a signal-storing-type noise elimination process (e.g., a bilateral filter), and an edge enhancing process, to each of the images in the CSF image sequence that is input to the CSF region specifying unit 126c or the like. Further, it is also possible to arbitrarily change, for each process, whether a noise elimination process is to be applied or not and the intensity level at which the noise elimination process is to be applied. For example, in the second embodiment, it is possible to make an arrangement so that a noise elimination process is applied to the process performed by the morphological region specifying unit 126f, whereas no noise elimination process is applied to the subsequent process performed by the CSF region specifying unit 126c.

Further, in the first and the second embodiments described above, the CSF image sequence that is input to the CSF region specifying unit 126c or the like may be made up of images to which a position alignment process (which may also be referred to as a "registration process") has been applied. As the position alignment process, it is possible to use any position alignment process such as a parallel displacement, a rotation, a zoom correcting process, or a warping process to align positions in units of pixels (which may be referred to as "Free Form Deformation (FFD)").

<Regarding Assigning the Colors>

In the first and the second embodiments described above, the CSF region and the morphological region are superimposed on the CSF image sequence after arranging these regions to be displayed in the specific colors. However, possible embodiments are not limited to this example. For example, the display controlling unit 126e may change the manner in which the CSF region is displayed in accordance with the levels of signal intensities of the pixels in the CSF region. For example, if the CSF image sequence transmitted from the CSF image generating unit 126b is made up of grayscale images, the display controlling unit 126e may color the CSF region by selecting a color for each of the pixels in such a manner that pixels within the CSF region having a higher level of signal intensity is displayed in "red", whereas pixels within the CSF region having a lower level of signal intensity is displayed in "blue". As another example, the display controlling unit 126e may obtain the highest value and the lowest value among the signal intensities of the pixels within the CSF region and may color the CSF region by selecting a color for each of the pixels in such a manner that "red" is assigned to the pixels having the highest value, whereas "blue" is assigned to the pixels having the lowest value, while the other pixels having intermediate signal intensities are displayed in corresponding colors so as to make a gradual transition from "red" to "blue". It is possible to display all the different levels of signal intensities in arbitrary colors by preparing the corresponding colors in a table (in the form of a color pallet) in advance.

<Regarding Examples of Displaying a Plurality of Types of Images and Examples of Displaying a Plurality of Imaging Regions>

In the first and the second embodiments described above, the example is explained in which the indexes derived by analyzing the CSF images of one type, as well as the CSF images of the one type are displayed on the display unit 125. However, possible embodiments are not limited to this example. It is acceptable to configure the MRI apparatus 100 according to the exemplary embodiments so as to derive indexes by analyzing each of CSF images which are of a plurality of types (e.g., CSF images from before surgery and after surgery) and which correspond to a plurality of time phases and to display, on the display unit 125, the derived indexes and the CSF images of the plurality of types.

Figure 20:
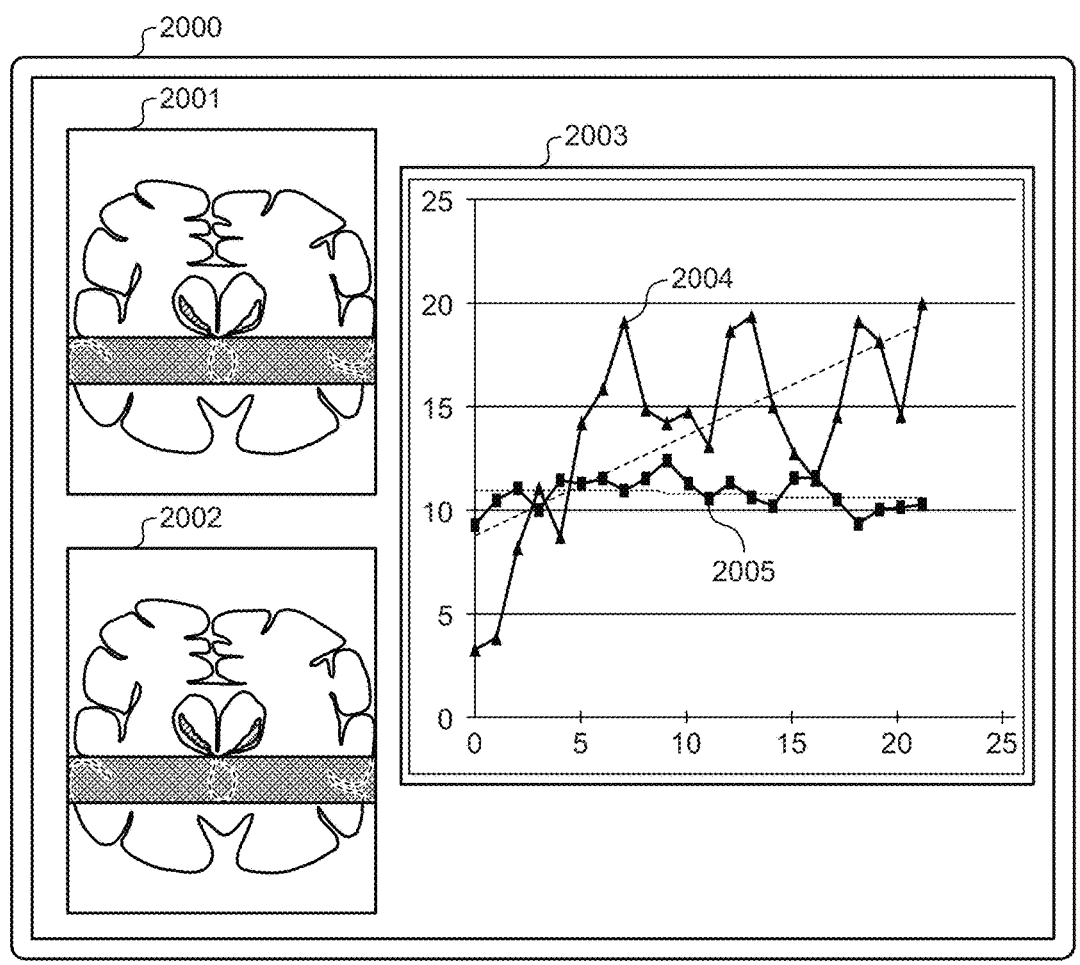
FIG. 20 is a drawing of an exemplary display according to yet another embodiment.

FIG. 20 is a drawing of an exemplary display according to yet another embodiment. For example, the display controlling unit 126e according to said another embodiment displays, as shown in FIG. 20, superimposed images 2001 corresponding to a CSF image sequence in a plurality of time phases acquired before surgery, for example, and superimposed images 2002 corresponding to a CSF image sequence in a plurality of time phases acquired after surgery, for example. Further, the display controlling unit 126e displays a plot line 2004 and a plot line 2005 corresponding respectively as well as regression lines corresponding respectively, in the same window 2003. When the CSF images of the plurality of types and the corresponding indexes are simultaneously displayed in this manner, it is easier for the viewer to make a comparison. Further, the superimposed images 2001, the superimposed images 2002, and the window 2003 do not necessarily have to be displayed simultaneously. It is acceptable to simultaneously display only one or two of these items.

Like in the first and the second embodiments, it is possible to arbitrarily select whether the superimposed images should be displayed or not, whether the superimposed images should be displayed as a moving picture or as still pictures, and whether the CSF region and/or the CSF position should be colored or not in the superimposed images.

In the example in FIG. 20, when displaying mutually the same site, the display controlling unit 126e may perform a normalization process or a position alignment process on the CSF image sequence by using the label region or the reference line used for calculating the distance. For example, if the reference line is not a straight line, and also, the shapes of the site rendered in the CSF image sequence of a plurality of types do not match each other, the display controlling unit 126e may deform each of the image sequences according to a straight line, by projecting or mapping the reference line onto the straight line for each of the CSF image sequences. In that situation, a site (e.g., the cerebral aqueduct) that is not rendered with straight lines will be rendered with straight lines as a result of the deformation of the images. It is therefore possible to improve visibility.

In the first and the second embodiments described above, the example is explained in which the indexes indicating the dynamics of the fluid are derived by analyzing each of the CSF images corresponding to the plurality of time phases and having been acquired from a "certain imaging region" inside the subject, so as to display the derived indexes and the CSF images. However, possible embodiments are not limited to this example. For example, to evaluate the dynamics of the CSF, the data acquiring unit 126a may acquire CSF images corresponding to a plurality of time phases from "a plurality of imaging regions" inside the same subject. In other words, for example, the MRI apparatus 100 according to the first embodiment is configured to acquire the CSF images corresponding to the plurality of time phases by using the sagittal plane of the brain as the imaging region and to derive the indexes by performing the analysis while using the acquired CSF images as the analyzed target. In contrast, it is also acceptable to configure the MRI apparatus 100 so as to, for example, acquire CSF images corresponding to a plurality of time phases from "a plurality of imaging regions" (e.g., a sagittal plane of the brain; a coronal plane of the brain; and an axial plane of the brain) of the same subject and to derive indexes by performing an analysis while using the acquired CSF images as the analyzed target.

Figure 21:
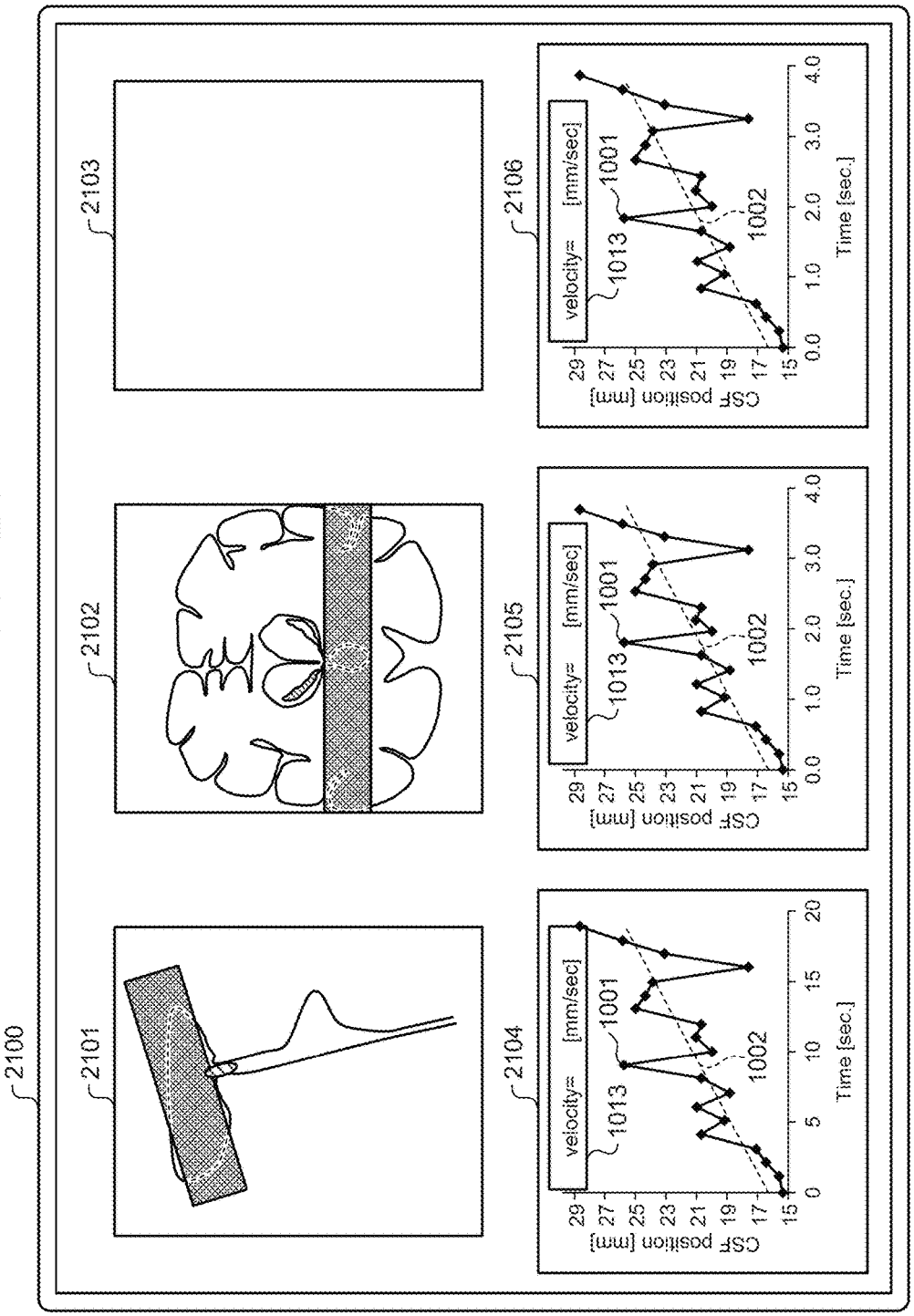
FIG. 21 is a drawing of an exemplary display according to yet another embodiment.

FIG. 21 is a drawing of an exemplary display according to yet another embodiment. For example, the display controlling unit 126e according to said another embodiment displays, as shown in FIG. 21, superimposed images 2101 corresponding to a CSF image sequence on a sagittal plane, superimposed images 2102 corresponding to a CSF image sequence on a coronal plane, and superimposed images 2103 (not shown) corresponding to a CSF image sequence on an axial plane that are arranged side by side. Further, the display controlling unit 126e displays a window 2104, a window 2105, and a window 2106 corresponding respectively. In addition, for example, the display controlling unit 126e may display, in the window 2104, the plot line 1001, the regression line 1002, and velocity information 1013, as necessary. When the CSF images and the indexes corresponding to the mutually-different imaging regions of mutually the same subject are simultaneously displayed in this manner, it is possible to have a high-angle view of the dynamics of the CSF.

Like in the first and the second embodiments, it is possible to arbitrarily select whether the superimposed images should be displayed or not, whether the superimposed images should be displayed as a moving picture or as still pictures, and whether the CSF region and/or the CSF position should be colored or not in the superimposed images. Further, the display controlling unit 126e does not necessarily have to simultaneously display all of the superimposed images and the windows. The display controlling unit 126e may display one or more of these items. Further, besides the example shown in FIG. 21, the MRI apparatus 100 may acquire CSF images from a plurality of imaging regions that are in a combination of clinical significance, may derive indexes for the imaging regions by performing an analysis while using the acquired CSF images as the analyzed target, and may display each of the derived indexes for the imaging regions. For example, the MRI apparatus 100 may acquire CSF images for a combination made up of a sagittal plane of the brain, a coronal plane of the brain, and a sagittal plane of the spine.

<Regarding Deriving the Indexes for a Plurality of Points in the CSF Region>

In the first and the second embodiments described above, the example is explained in which the position at one point (e.g., the lower end point having the longest distance from the reference position) within the CSF region is determined to be the CSF position so that the locus of the moving of the CSF position is traced by performing the analysis. However, possible embodiments are not limited to this example. It is acceptable to determine a plurality of points within the CSF region to be CSF positions and to trace the locus of the moving of each of the points over the CSF images corresponding to a plurality of time phases by performing an analysis.

Figure 22:
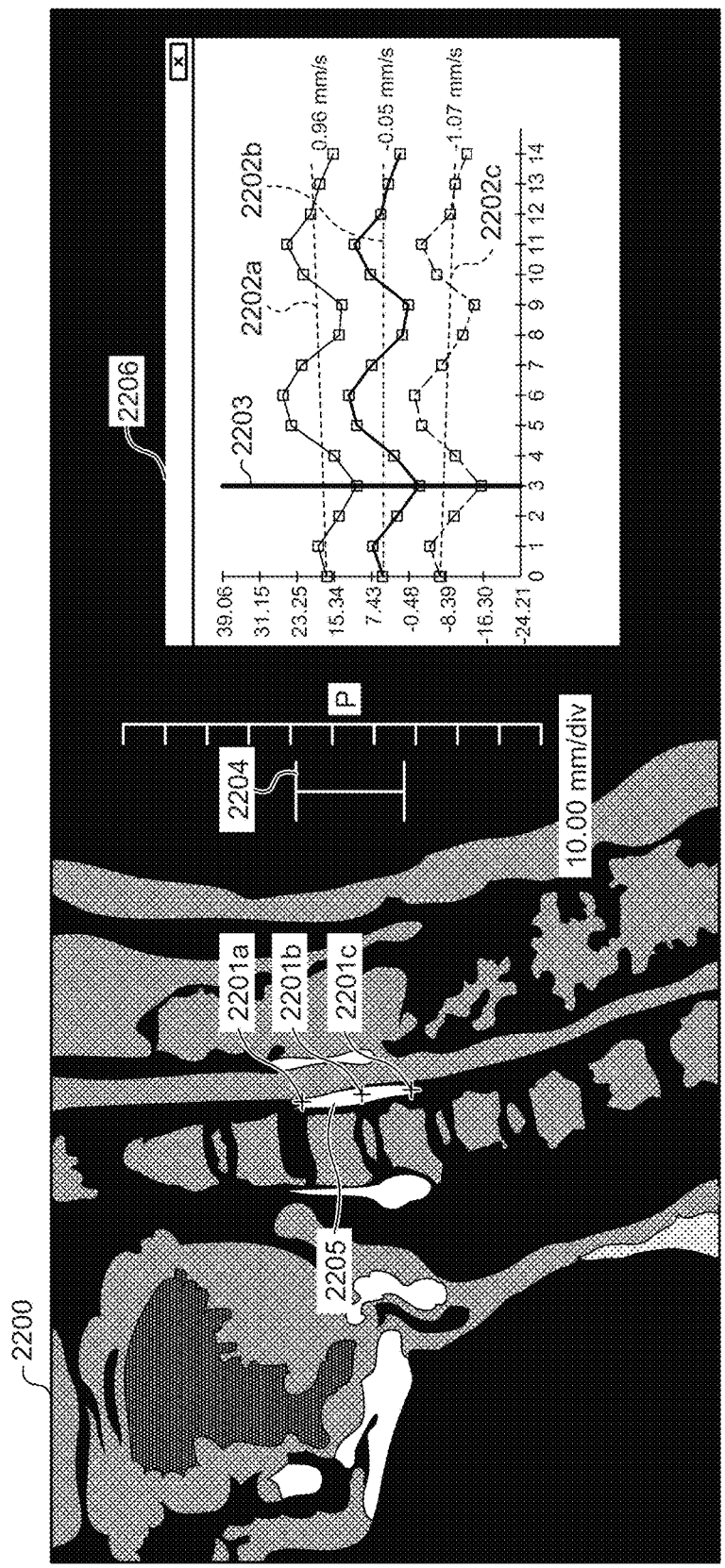
FIG. 22 is a drawing of an exemplary display according to yet another embodiment.

FIG. 22 is a drawing of an exemplary display according to yet another embodiment. Although FIG. 22 illustrates an exemplary display, FIG. 22 will also be used for explaining a process performed by the index deriving unit 126d below, for the sake of convenience in explanation. As shown in FIG. 22, for example, the index deriving unit 126d specifies an upper end point 2201a, a lower end point 2201c, and a middle point 2201b that represent a CSF region 2205, as CSF positions. After that, by performing an analysis on each of the CSF images corresponding to a plurality of time phases, the index deriving unit 126d derives indexes by specifying the distance from a predetermined reference position (e.g., the middle point 2201b in the frame corresponding to the first time phase), with respect to each of the upper end point 2201a, the middle point 2201b, and the lower end point 2201c. The method for specifying the CSF positions and the method for calculating the distances are the same as those described in the first and the second embodiments. The plurality of points selected as the CSF positions do not necessarily have to be the three points such as the upper end point, the middle point, and the lower end point. The number of points is arbitrary and may be two or four. The positions do not have to be the upper end point, the middle point, and the lower end point; it is acceptable to select any arbitrary positions. Further, the index deriving unit 126d may derive, as one of the indexes, the distance from the upper end point to the lower end point (e.g., the span of the CSF region).

After that, the display controlling unit 126e displays the indexes that were derived by the index deriving unit 126d with respect to each of the upper end point 2201a, the middle point 2201b, and the lower end point 2201 and displays, on the display unit 125, the CSF images in which the CSF positions and the CSF region are displayed in a superimposed manner. For example, as shown in FIG. 22, the display controlling unit 126e displays, on the display unit 125, superimposed images in which the upper end point 2201a, the middle point 2201b, the lower end point 2201c, and the CSF region 2205 are displayed in a superimposed manner, so as to be arranged side by side with a plot chart 2206.

In this situation, the display controlling unit 126e displays, in the superimposed image, the upper end point 2201a, the middle point 2201b, and the lower end point 2201c, by using a symbol "+", for example. Also, the display controlling unit 126e displays a bar 2204 that connects together the upper end point and the lower end point of the CSF region 2205. Further, the display controlling unit 126e displays, in the plot chart 2206, a plot line and a regression line 2202a corresponding to the upper end point 2201a, a plot line and a regression line 2202b corresponding to the middle point 2201b, and a plot line and a regression line 2202c corresponding to the lower end point 2201c. In addition, as shown in FIG. 22, the display controlling unit 126e further displays, in the plot chart 2206, a line 2203 indicating the frame number of the frame currently being displayed or a time. Like in the first and the second embodiments, the X-axis may express, for example, a time starting with the point in time at which the first frame was acquired or an elapsed time period starting with a TI period, instead of the frame numbers. Further, the Y-axis may express the area size of the CSF region instead of the CSF position.

The exemplary display explained with reference to FIG. 22 is merely an example. The display controlling unit 126e may select the information to be displayed as appropriate, in accordance with the mode of operation or the like. For example, any arbitrary symbol can be used for indicating the CSF position. Further, although the CSF positions are typically arranged at the end points and the middle point of the CSF region as mentioned above, possible arrangements are not limited to this example. It is acceptable to arrange the CSF positions at any arbitrary positions. Further, it is acceptable to display, by using any arbitrary method, an arbitrary quantity of CSF positions (e.g., only the middle point or only the upper end point) from among the plurality of CSF positions.

<Regarding Other Exemplary Displays>

Figure 23:
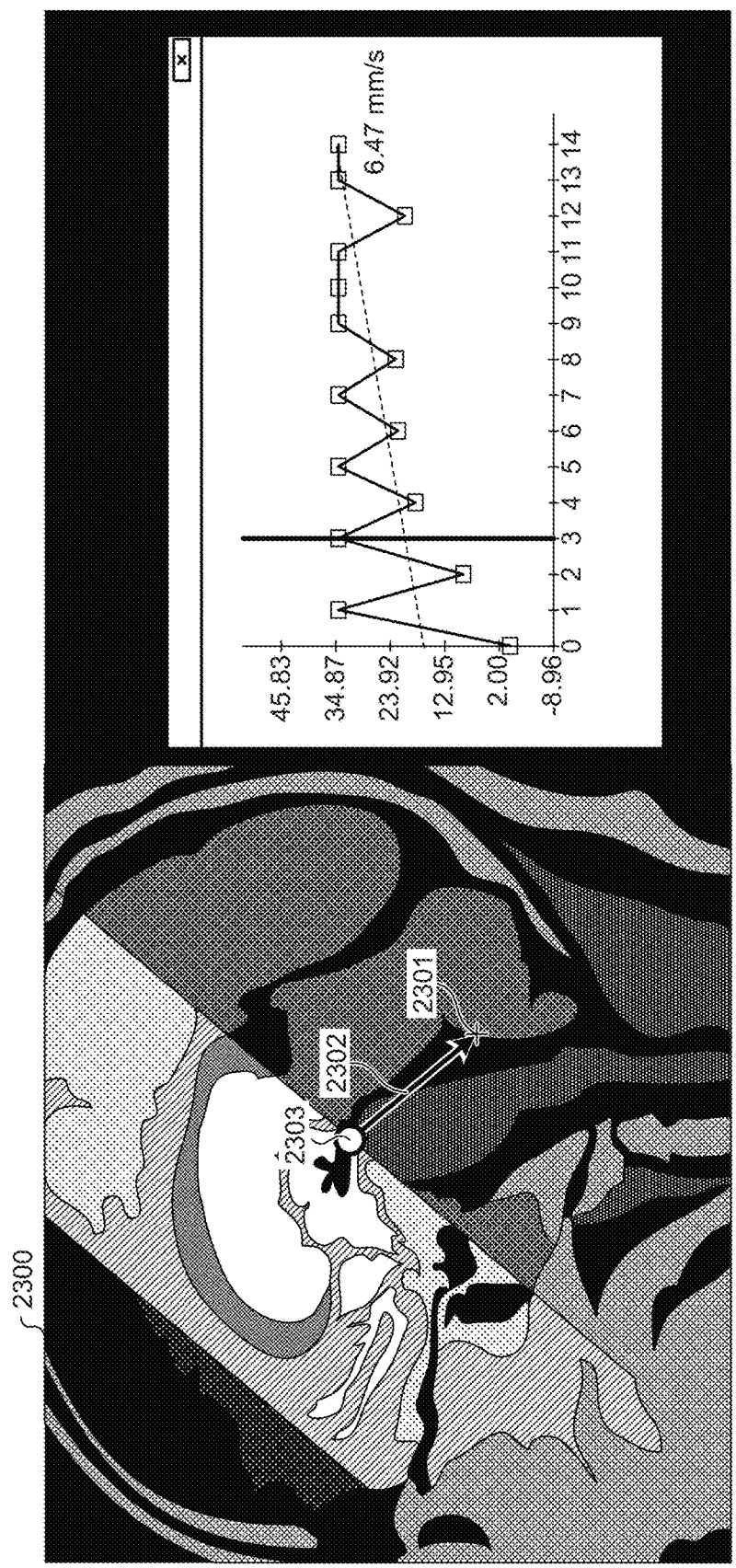
FIG. 23 is a drawing of an exemplary display according to yet another embodiment.

FIG. 23 is a drawing of an exemplary display according to yet another embodiment. For example, when displaying the superimposed images on the display unit 125, the display controlling unit 126e may display an arrow 2302 connecting a reference position 2303 to a CSF position 2301, as shown in FIG. 23. In that situation, for example, the display controlling unit 126e may display the superimposed images as a moving picture and may switch the display of the arrow 2302 in accordance with the switching from the CSF image to the CSF image in the next time phase.

It is also acceptable to configure the MRI apparatus 100 according to yet another embodiment to exercise control so that the imaging process is re-performed depending on results of the CSF region specifying process or the derived indexes. If the CSF region was not properly specified or if any of the indexes like the velocity information exceeds a predetermined range, the MRI apparatus 100 may display a message to inform the operator of the situation and may prompt the operator to re-perform the imaging process or to take images with different timing.

Figure 24:
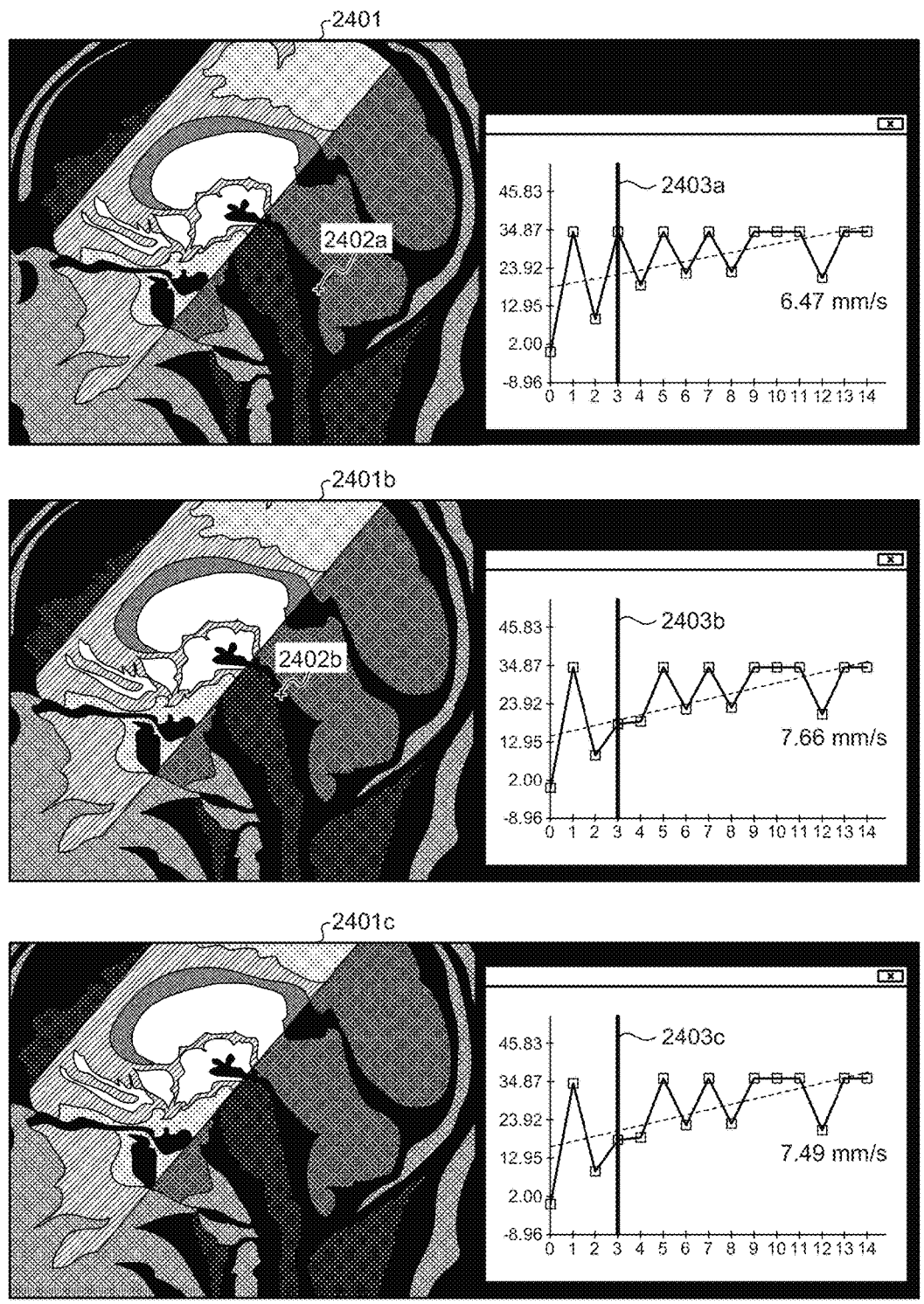
FIG. 24 is a drawing of a correction and a deletion according to said another embodiment.

FIG. 24 is a drawing of a correction and a deletion according to said another embodiment. FIG. 24 illustrates three exemplary displays. In the exemplary display at the top, a CSF position 2402a in one frame is displayed by using the symbol "+" while being superimposed on the CSF image, and also, a corresponding plot point 2403a is displayed in the plot chart (using a bar). In this situation, the display controlling unit 126e may receive a correction of the CSF position to be displayed or a deletion of the CSF position, by receiving specifications of the CSF position 2402a and the plot point 2403a from the operator using an arbitrary method such as via a mouse. The exemplary display in the middle of FIG. 24 illustrates an example in which the CSF position 2402a has been corrected to a new CSF position 2402b. In this situation, the display controlling unit 126e may correct the plot point 2403a so as to correspond to the new CSF position 2402b. Conversely, the display controlling unit 126e may receive an instruction that the plot point 2403a should be changed to a plot point 2403b, for example. In that situation, the display controlling unit 126e may change the CSF position 2402a to the CSF position 2402b so as to be compliant with the change.

Further, the exemplary display at the bottom of FIG. 24 illustrates an example in which the CSF position 2402a is deleted. For example, when having received an instruction to delete the CSF position 2402a in the CSF image, the display controlling unit 126e may also delete the plot point 2403a that corresponds to the deleted CSF position 2402a. In other words, the plot point positioned at 2403c in FIG. 24 shall be deleted.

<Specifying a Morphological Region by Using a Signal Transition>

In the second embodiment described above, the example is explained in which, the morphological region is first specified, and the CSF region of the "labeled" CSF is further specified within the specified morphological region. In the following sections, as another example of these processes performed in two stages, an example will be explained in detail in which a CSF region where CSF is simply present is specified regardless of whether the CSF is labeled or not, and subsequently, a CSF region of the "labeled" CSF is specified within the specified region.

Figure 25:
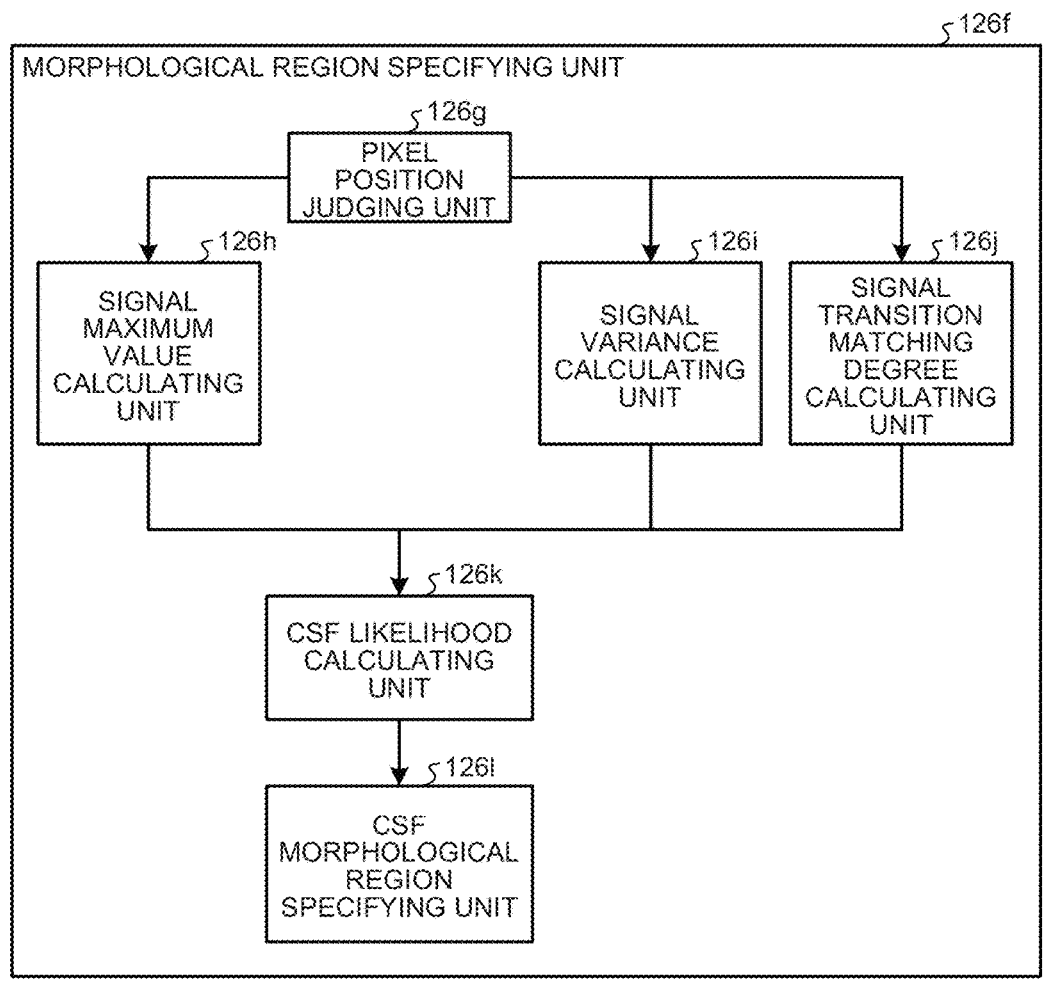
FIG. 25 is a block diagram of a morphological region specifying unit according to an embodiment.

FIG. 25 is a block diagram of the morphological region specifying unit 126f according to yet another embodiment. As shown in FIG. 25, the morphological region specifying unit 126f includes a pixel position judging unit 126g, a signal maximum value calculating unit 126h, a signal variance calculating unit 126i, a signal transition matching degree calculating unit 126j, a CSF likelihood calculating unit 126k, and a CSF morphological region specifying unit 126l.

The pixel position judging unit 126g is configured to receive CSF images corresponding to a plurality of time phases and to judge the pixel position of each of the pixels as to whether the pixel is in a label region or outside a label region. The position information of the label region is information that is set at the stage of planning the imaging process. Thus, for example, the pixel position judging unit 126g obtains the position information of the label region from the storage unit 123 storing therein the imaging conditions and judges the pixel position of each of the pixels on the basis of the obtained position information.

The signal maximum value calculating unit 126h is configured to, with respect to the pixels that were each judged to be a pixel in the label region by the pixel position judging unit 126g, analyze the CSF images over the plurality of time phases and to obtain the maximum value of signal intensity among the plurality of time phases.

The signal variance calculating unit 126i is configured to, with respect to the pixels that were each judged to be a pixel outside the label region by the pixel position judging unit 126g, analyze the CSF images over the plurality of time phases so as to calculate a quantitative value indicating the mode of transition of the signal intensity in the time direction (i.e., a value that quantitatively indicates how the signal intensity goes through a transition over the course of time). For example, the signal variance calculating unit 126i calculates a variance. For example, if the variance is large, it means that the signal intensity repeatedly goes up and down frequently, for example. Thus, in the present example, it is assumed that there is a high possibility that a large variance value indicates a region where the labeled CSF went back and forth. Consequently, it is assumed that the higher the variance is, the higher the probability of the pixel representing the CSF.

The signal transition matching degree calculating unit 126j is configured to, with respect to the pixels that were each judged to be a pixel outside the label region by the pixel position judging unit 126g, analyze the CSF images over the plurality of time phases so as to calculate a matching degree indicating the degree of matching as to whether the CSF is represented or not. In this situation, the signal transition matching degree calculating unit 126j calculates the matching degree by using expression (6) below:

$$T_p = \sum_{f=1}^{F} t_p(f) \quad (6)$$

$$t_p(f) = \begin{cases} 1, & \text{if } f < f_n \text{ and } S_{f,p} < S_{f-1,p} \\ 1, & \text{if } f > f_n \text{ and } S_{f,p} > S_{f-1,p} \\ 0, & \text{else} \end{cases}$$

Expression (6) is used for calculating the probability of each of the pixels representing the CSF, while focusing on the characteristics indicating how the signal intensity of the "unlabeled" CSF goes through a transition over the course of time.

Figure 26:
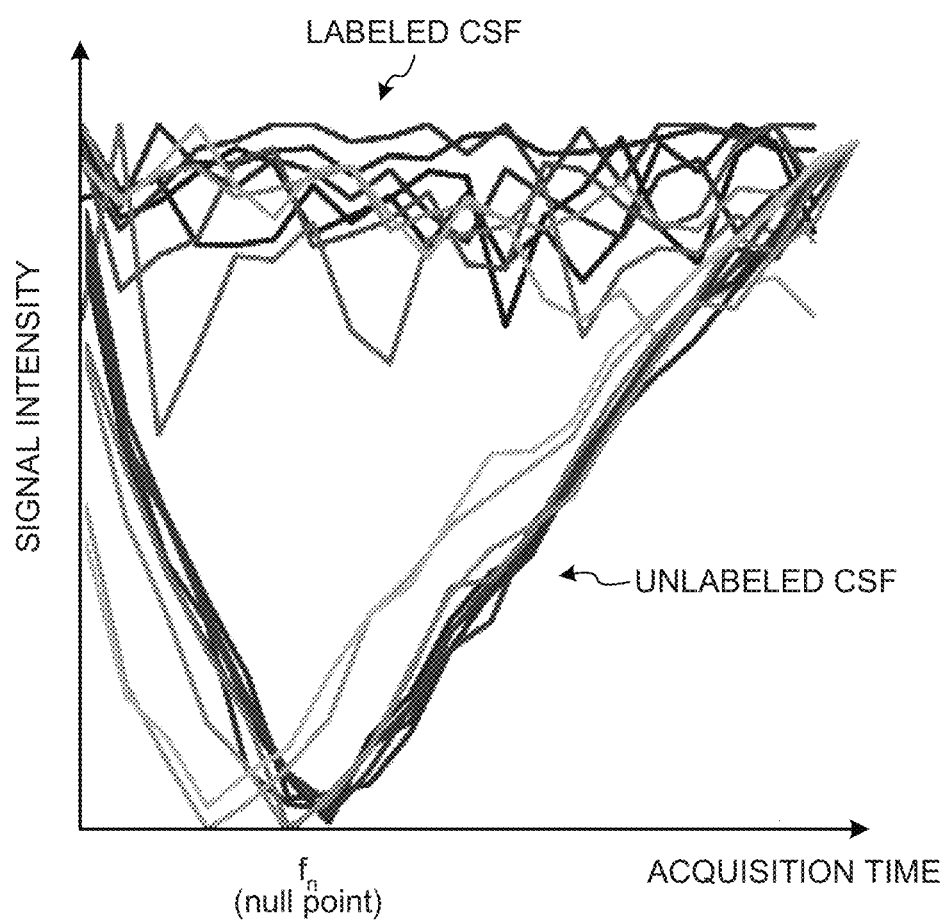
FIG. 26 is a chart for explaining characteristics of a transition of a signal intensity of CSF.

FIG. 26 is a chart for explaining the characteristics of the transition of the signal intensity of the CSF. As explained with reference to FIG. 3, when the t-SLIP method is used, typically, the non-region-selecting IR pulse and the region-selecting IR pulse are both applied substantially at the same time. FIG. 26 indicates, for each of the pixels, the transition of the signal intensity that is observed when the IR pulses are applied substantially at the same time. In this situation, with regard to the CSF (the "labeled CSF") to which both of the two IR pulses were applied within the label region, the signal intensity goes through a transition while maintaining a rather high value, as shown in FIG. 26, because the longitudinal magnetic component is first inversed by applying the non-region-selecting IR pulse, and subsequently, the longitudinal magnetic component is inversed again by applying the region-selecting IR pulse. In contrast, with regard to the CSF (the "unlabeled CSF") to which only the non-region-selecting IR pulse was applied on the outside of the label region, the longitudinal magnetic component is first inversed by applying the non-region-selecting IR pulse, and subsequently, the longitudinal magnetic component is gradually restored. As shown in FIG. 26, in this situation, the signal intensity, which is expressed with an absolute value, decreases substantially monotonously during the restoration process and, after reaching a null point which corresponds to a T1 value of the CSF and at which the longitudinal magnetization become "0", the signal intensity increases again substantially monotonously. In the chart, the frame "$f_n$" denotes the frame having the smallest longitudinal magnetic component (an absolute value).

In Expression (6), "p" denotes a pixel, whereas "f" denotes a frame. In this situation, for each of the frames earlier than the frame $f_n$ in terms of the time direction, "$t_p(f)$" is equal to "1", if the signal intensity in the frame is lower than the signal intensity in the immediately preceding frame. This situation corresponds to the monotonous decrease shown in FIG. 26. Further, for each of the frames later than the frame $f_n$ at the null point in terms of the time direction, "$t_p(f)$" is equal to "1", if the signal intensity in the frame is higher than the signal intensity in the immediately preceding frame. This situation corresponds to the monotonous increase shown in FIG. 26. If neither of these conditions is satisfied, "$t_p(f)$" is equal to "0".

The matching degree "$T_p$" of each of the pixels is a total value obtained by adding up the "$t_p(f)$" values in the time direction. The higher the value "$T_p$" is, the higher is the probability of the pixel representing the CSF.

In another example of a method for deriving a matching degree, the matching degree may be expressed as a difference from a signal transition model of the CSF. For example, the signal transition matching degree calculating unit 126j may calculate a matching degree by using Expression (7) or Expression (8) shown below.

$$t_p(f) = \text{abs}(S_{f,p} - O_f) \quad (7)$$

$$t_p(f) = (S_{f,p} - O_f)^2 \quad (8)$$

In these expressions, "$O_f$" denotes a signal transition model of the CSF in frame f, whereas "$t_p$" denotes the difference (an error) calculated by using an absolute value error (Expression (7)) or a square error (Expression (8)).

The CSF likelihood calculating unit 126k is configured to calculate a CSF likelihood value for each of the pixels by using the values obtained by the signal maximum value calculating unit 126h, the signal variance calculating unit 126i, and the signal transition matching degree calculating unit 126j.

In this situation, for example, the CSF likelihood calculating unit 126k calculates a CSF likelihood value by using Expression (9) below.

$$L_p = \alpha_p S_{m,p} + (1-\alpha_p)(\beta S_{v,p} + (1-\beta)T_p) \quad (9)$$

In Expression (9), the coefficients "$\alpha_p$" and "$1-\alpha_p$" reflect the judgment results from the pixel position judging unit 126g. In other words, if the pixel position judging unit 126g has determined the pixel to be a pixel in the label region, "$\alpha_p=1$" is satisfied, so that only the first term on the right side of Expression (9) is reflected in the calculation of the CSF likelihood value. On the contrary, if the pixel position judging unit 126g has determined the pixel to be a pixel outside the label region, "$\alpha_p=0$" is satisfied, so that only the second term on the right side of Expression (9) is reflected in the calculation of the CSF likelihood value.

Further, "$S_{m,p}$" in the first term is the maximum value of signal intensity calculated by the signal maximum value calculating unit 126h, whereas "$S_{v,p}$" in the second term is the variance calculated by the signal variance calculating unit 126i. Further, "$T_p$" in the second term denotes the matching degree calculated by the signal transition matching degree calculating unit 126j. The weighting factor "β" for a linear sum of the variance and the matching degree is set appropriately.

The larger the CSF likelihood value calculated by using Expression (9) is, the higher is the likelihood of the pixel representing the CSF.

The CSF morphological region specifying unit 126l specifies a CSF region by performing, for example, a threshold operation on the CSF likelihood value calculated by the CSF likelihood calculating unit 126k. In this situation, the CSF region may be represented by multiple regions that are positioned slightly away from one another. Thus, the CSF morphological region specifying unit 126l further performs an image processing process such as a region glowing process on the specified CSF region. The CSF region that has thus been specified by the CSF morphological region specifying unit 126l is a CSF region where the CSF is simply present, regardless of whether the CSF is labeled or not.

Figure 27:
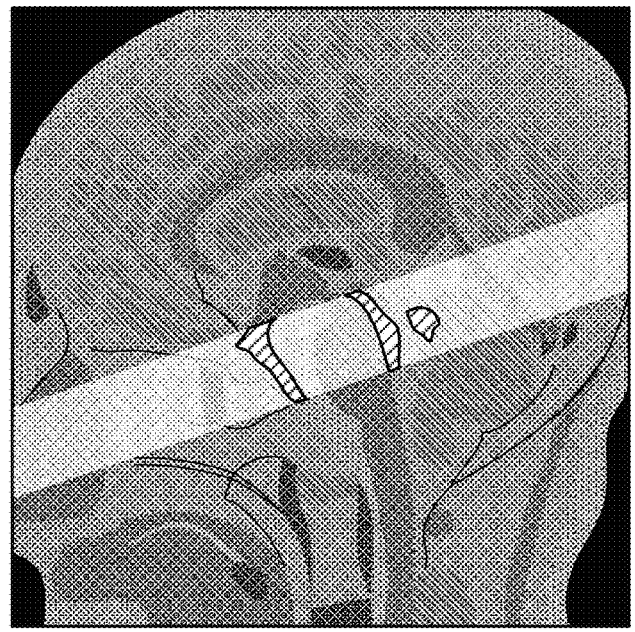
FIG. 27 is a drawing of CSF that has been labeled in a label region.
Figure 28:
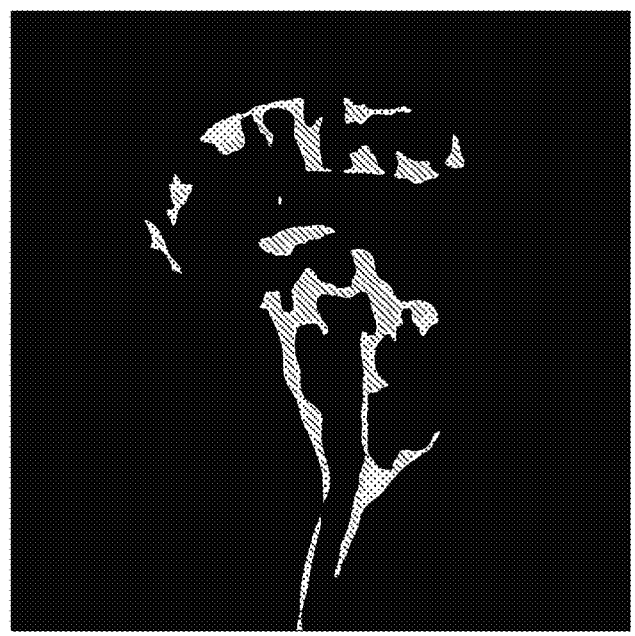
FIG. 28 is a drawing of a morphological region specified by the morphological region specifying unit.

FIG. 27 is a drawing of CSF that has been labeled in a label region. In FIG. 27, for the sake of convenience in explanation, the CSF that has been labeled and has a high signal intensity is indicated by superimposing a pattern thereon. FIG. 28 is a drawing (a map) of a morphological region specified by the morphological region specifying unit 126f. The morphological region illustrated in FIG. 28 includes a "labeled" CSF region and an "unlabeled" CSF region; however, the "labeled" and "unlabeled" CSF regions are not distinguished from each other at this stage where the region was specified as a morphological region.

After that, for example, the CSF region specifying unit 126c explained in the exemplary embodiments above specifies a CSF region of the "labeled" CSF, from the CSF region specified in this manner.

For example, as understood from FIG. 26, there is a significant difference (a contrast) in the signal intensities between the "labeled" CSF and the "unlabeled" CSF, in at least a certain range near the null point of the CSF. Thus, the CSF region specifying unit 126c performs, for example, a threshold operation based on the difference in the signal intensities on the CSF region specified as the morphological region so as to realize segmentation between the CSF region of the "labeled" CSF and the CSF region of the "unlabeled" CSF.

Expressions (6) to (9) presented above may be modified as necessary. For example, Expression (9) may be modified so that the variance of each of the pixels in the label region is also reflected in the judgment on the likelihood of the pixel representing the CSF.

Further, it is also acceptable to modify Expression (9) so that a result of a spatial structure judgment is reflected in the judgment made with Expression (9). An example of the structure judgment can be based on an edge enhancement. Because a location having a high level of edge enhancement is considered to be a boundary with a structure in the body of the subject, the likelihood of the location representing the CSF is low. In contrast, because a location having a low level of edge enhancement is considered to be the inside of a structure in the body of the subject, the likelihood of the location representing the CSF is high. Alternatively, it is also acceptable to use an Active Counter Model (ACM) or an Active Shape Model (ASM).

Further, it is also acceptable to apply, in advance, a smoothing process or an edge enhancement process to each of the pixels of which the signal intensity maximum value, the variance, and the matching degree are to be calculated.

In the example explained above, the functional units included in the morphological region specifying unit 126f perform the processes for each of the pixels; however, possible embodiments are not limited to this example. A part or all of the functional units included in the morphological region specifying unit 126f may perform the processes for each of image regions that each include two or more pixels.

<Displaying the CSF and Background Tissues Separately in the Label Region>

As explained above, for each of the pixels in the label region, it is possible to determine if a target pixel represents the CSF or background tissues other than the CSF, by analyzing the CSF image over the plurality of time phases and calculating the maximum value of signal intensity among the plurality of time phases.

Accordingly, the index deriving unit 126d is also able to use the CSF in the label region as a target of the index deriving process. Further, when displaying the CSF position and the CSF region so as to be superimposed on the CSF images, the display controlling unit 126e is also able to display the CSF region in the label region, together with the CSF region outside the label region, in a superimposed manner.

Figure 29:
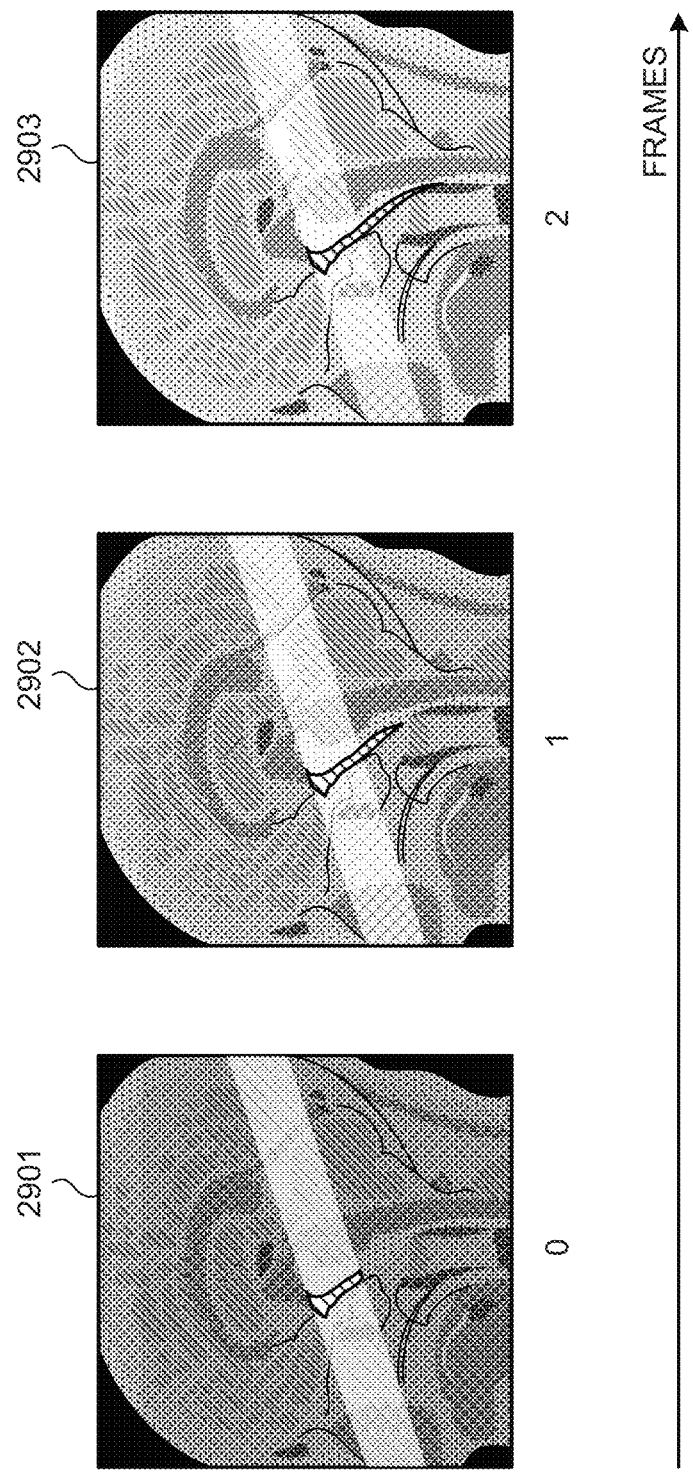
FIG. 29 is a drawing of exemplary displays according to yet another embodiment.

FIG. 29 is an exemplary display according to yet another embodiment. For example, when displaying the CSF images as in the exemplary display shown in FIG. 11, the display controlling unit 126e assigns, as shown in FIG. 29, one color to the CSF that is positioned in the label region and has been labeled and to the CSF that is positioned outside the label region and has been labeled and further displays, for example, these areas as one continuous CSF region in a superimposed manner.

In the example explained above, the one color is assigned to the superimposed CSF region; however, possible embodiments are not limited to this example. For example, it is also acceptable to assign mutually-different colors to the inside and to the outside of the label region.

<Setting a Range of Imaging Timing>

Figure 30:
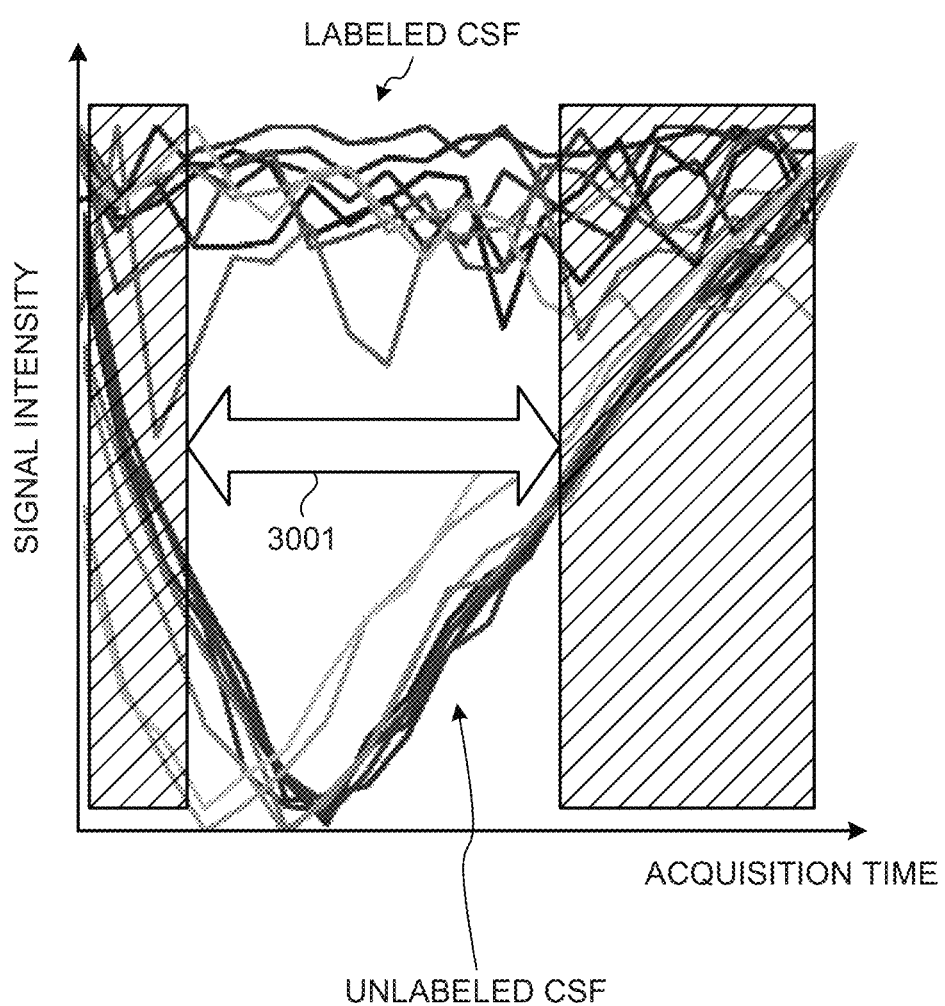
FIG. 30 is a drawing for explaining setting a range of imaging timing.

FIG. 30 is a drawing for explaining setting a range of imaging timing. As explained with reference to FIG. 26, the difference in the signal intensities between the "labeled" CSF and the "unlabeled" CSF is largest near the null point of the CSF. Thus, for example, the data acquiring unit 126a may be configured to limit the imaging timing to a certain range (the range indicated by a white bold arrow in FIG. 30) near the null point, as shown in FIG. 30, while using the null point of the CSF as a reference.

Figure 31:
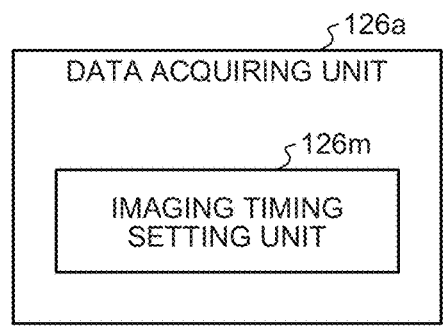
FIG. 31 is a diagram of a data acquiring unit according to yet another embodiment.

FIG. 31 is a diagram of the data acquiring unit 126a according to yet another embodiment. The data acquiring unit 126a further includes an imaging timing setting unit 126m. The imaging timing setting unit 126m displays, on the display unit 125, a Graphical User Interface (GUI) used for receiving a setting of an imaging timing range from the operator and receives the setting of the imaging timing range. After that, the data acquiring unit 126a acquires data in the imaging timing range of which the setting was received by the imaging timing setting unit 126m. The GUI is typically displayed on the display unit 125 at the regular stage of planning an imaging process.

Figure 32:
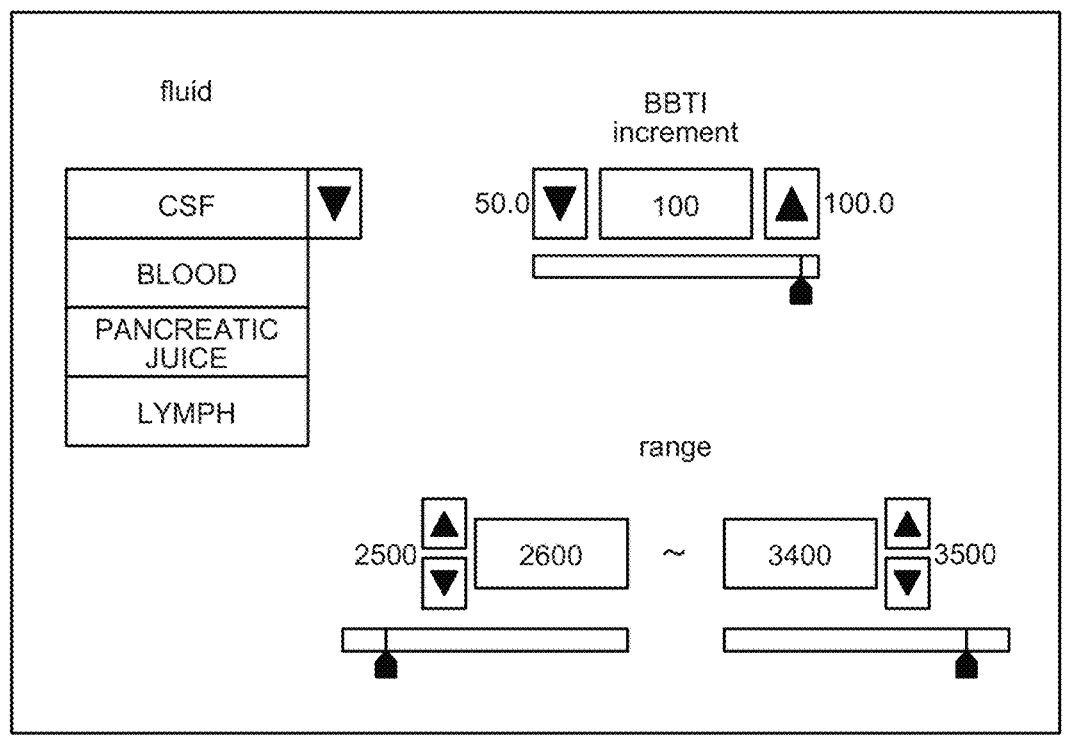
FIG. 32 is a drawing for explaining a Graphical User Interface (GUI) used for receiving a setting of an imaging timing range.

FIG. 32 is a drawing for explaining the GUI used for receiving a setting of an imaging timing range.

For example, the imaging timing setting unit 126m displays a GUI used for receiving the type of the fluid ("fluid") selected as an imaging target, an increment ("BBTI increment") for Black-Blood Time to Inversion (BBTI) periods, and a range ("range") in which the BBTI periods are set. In this situation, a "BBTI period" denotes a time period between when an IR pulse is applied and when a data acquisition is started. The increment for BBTI periods denotes the difference between "TI1" and "TI2" explained with reference to FIGS. 4A and 4B, for example. The "range in which the BBTI periods are set" denotes a range from a BBTI period of the first time phase to a BBTI period of the last time phase, in the situation where CSF images corresponding to a plurality of time phases are acquired.

For example, in accordance with the type of the fluid selected at the stage of planning an imaging process, the imaging timing setting unit 126m changes, in the GUI, the lower limit value and the upper limit value of a range that can be used for setting the BBTI periods. For example, if "CSF" is selected as the fluid serving as an imaging target, the imaging timing setting unit 126m displays, in the GUI, a lower limit value and an upper limit value that are compliant with the T1 value (the TI period to the null point) of "CSF" and will not receive any settings outside the range. For example, if the T1 value of CSF is "3000 msec", the imaging timing setting unit 126m displays a lower limit value "2500" and an upper limit value "3500" or the like, as shown in FIG. 32, and only receives settings that are in this range.

Further, if "blood" is selected as the fluid serving as an imaging target, for example, the imaging timing setting unit 126m displays, in the GUI, a lower limit value and an upper limit value that are compliant with the T1 value (e.g., "1200") of "blood" and will not receive any settings outside the range. Generally speaking, the T1 value of CSF is longer, and the T1 value of blood is shorter.

In the explanation above, the method is explained by which the settings outside the lower limit value and the upper limit value will not be received; however, possible embodiments are not limited to this example. It is acceptable, for example, to display an alert when a setting that is outside of the lower limit or the upper limit is selected.

Further, in the explanation above, the method is explained by which the imaging timing is limited to the certain range near the null point of CSF, by focusing on the difference in the signal intensities between the "labeled CSF" and the "unlabeled" CSF. However, possible embodiments are not limited to this example.

For example, in the first embodiment, the example is explained in which the CSF region where the labeled CSF is present is specified directly, without going through the stage of specifying a morphological region. In that situation, it may be considered desirable if there is a significant difference in the signal intensities between the labeled CSF region and other background tissues.

For this reason, for example, the imaging timing setting unit 126m may be configured to limit the imaging timing range to a certain range near the null point of the background tissues, by using the null point of the background tissues as a reference, instead of the null point of CSF. In this situation, the background tissues are the cerebral aqueduct and the fourth ventricle, for example.

<Others>

In the exemplary embodiments described above, the example is explained in which the images taken by the MRI apparatus 100 are used; however, possible embodiments are not limited to this example. For example, the various types of processes described above are similarly applicable to situations where the images are taken by other medical image diagnosis apparatuses such as X-ray Computed Tomography apparatuses, X-ray diagnosis apparatuses, and ultrasound diagnosis apparatuses. In other words, the various types of processes described above are similarly applicable to situations where any other medical image diagnosis apparatus takes a plurality of images that render a fluid flowing through the body of a subject and that are mutually related.

Further, in the exemplary embodiments described above, the example is explained in which the MRI apparatus 100, which is a medical image diagnosis apparatus, performs the various types of processes; however, possible embodiments are not limited to this example. For example, it is acceptable if an image processing apparatus or an image display apparatus performs the various types of processes described above, in place of the MRI apparatus 100. In this situation, examples of the image processing apparatus and the image display apparatus include work stations, image storing apparatuses (image servers) and viewing tools in Picture Archiving and Communication Systems (PACS), and various types of apparatuses in electronic medical record systems. In that situation, for example, the image processing apparatus or the image display apparatus receives the plurality of images acquired by the MRI apparatus 100 from the MRI apparatus 100 or by receiving the images from an image server via a network or by receiving inputs of images from the operator via a recording medium. After that, the image processing apparatus or the image display apparatus performs the various types of processes described above while using the received plurality of images as a processing target. In the exemplary embodiments described above, the example is explained in which the superimposed images and the plot charts are displayed on the display unit 125; however, possible embodiments are not limited to this example. After the indexes have been derived, it is acceptable to end the process without displaying the indexes. In that situation, for example, the indexes derived by an image processing apparatus are used by another apparatus.

The exemplary embodiments are explained by using CSF as an example of the fluid flowing through the body of the subject; however, possible embodiments are not limited to this example. The fluid may be blood, pancreatic juice, or lymph, for example.

Further, the instructions indicated in the processing procedures in the exemplary embodiments described above may be executed on the basis of a computer program (hereinafter, "program") in the form of software. By causing a generally-used computer system to store therein such a program in advance and causing the computer system to read the program, it is possible to achieve the same advantageous effects as those of the MRI apparatus 100 according to the exemplary embodiments described above. The instructions described in the exemplary embodiments above are recorded as a computer-executable program, onto a magnetic disk (e.g., a flexible disk, a hard disk), an optical disk (e.g., a Compact Disk Read-Only Memory (CD-ROM), a Compact Disk Recordable (CD-R), a Compact Disk Rewritable (CD-RW), a Digital Versatile Disk Read-Only Memory (DVD-ROM), a Digital Versatile Disk Recordable (DVD±R), a Digital Versatile Disk Rewritable (DVD±RW)), a semiconductor memory, or any other similar recording medium. As long as the recording medium is readable by a computer or an incorporated system, any recording format may be used. When the computer reads the program from the recording medium and causes a CPU to execute the instructions written in the program according to the program, the computer is able to realize the same operations as those of the MRI apparatus 100 according to the exemplary embodiments. Needless to say, when the computer obtains or reads the program, the program may be obtained or read via a network.

An operating system (OS) working on a computer, database management software, or middleware (MW) such as a network may perform a part of the processes that realize the exemplary embodiments described above, according to the instructions in the program installed from the recording medium into the computer or an incorporated system.

Further, the recording medium realizing the exemplary embodiments is not limited to a medium that is independent of a computer or an incorporated system, but may be a recording medium that has stored therein or that is temporarily storing therein the program transferred through a Local Area Network (LAN) or the Internet and downloaded. It is acceptable to store the program that realizes the processes described in the exemplary embodiments into a computer (a server) connected to a network such as the Internet and to cause another computer (a client) to download the stored program via the network. The recording medium does not necessarily have to be one. The situation in which the processes described in the exemplary embodiments are executed from two or more media is also included in the examples of recording media realizing the exemplary embodiments. Any configuration of recording medium or recording media is acceptable.

The computer or the incorporated system realizing the exemplary embodiments is used for executing the processes described in the exemplary embodiments, according to the program stored in a recording medium or recording media. Thus, the computer or the incorporated system may have any configuration and may be configured with a single apparatus such as a personal computer or a microcomputer or may be configured with a system in which two or more apparatuses are connected together via a network. Further, the computer realizing the exemplary embodiments does not necessarily have to be a personal computer and may be an arithmetic processing unit included in an information processor or a microcomputer. The term "computer" generally refers to all devices and apparatuses that are able to realize the functions in the exemplary embodiments described above, according to the program.

It is possible to use any of the exemplary embodiments described above in combination, as necessary. For example, what is displayed by the display controlling unit 126e on the display unit 125 may be obtained by combining together any of the displays in any of the exemplary embodiments as necessary, depending on the mode of operation.

According to at least one aspect of the image processing apparatus, the image display apparatus, and the magnetic resonance imaging apparatus and method described in the exemplary embodiments, it is possible to appropriately evaluate the dynamics of the fluid in the body of the subject.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus comprising:
    at least one computer connected to communicate with memory storing (a) a plurality of magnetic resonance images acquired from a subject representing anatomical structures having fluid portions therewithin and (b) executable computer program instructions which, when executed by said at least one computer;
    specify a fluid region which is a region corresponding to a fluid portion of a subject in a plurality of magnetic resonance images that were acquired by applying a labeling pulse to a label region and that are mutually related;
    derive a plurality of index values indicating dynamics of a fluid based on the specified fluid region in the images and derive a velocity of the fluid based on the index values, wherein
    the dynamics include the fluid repeatedly moving forward and backward or the fluid repeatedly diffusing and contracting during the time data defining the images was acquired; and
    display a graph plotting the index values against time and the derived velocity, wherein each index value of the graph indicates the dynamics of the fluid repeatedly moving forward and backward or the dynamics of the fluid repeatedly diffusing and contracting.

2. The image processing apparatus according to claim 1, wherein the specified fluid region includes a labeled fluid region corresponding to a fluid labeled by the labeling pulse, and a non-labeled fluid region corresponding to a fluid not labeled by the labeling pulse.

3. The image processing apparatus according to claim 2 wherein, the labeled fluid region is further specified in the fluid region.

4. The image processing apparatus according to claim 2, wherein the fluid region is specified in displayed cross-sectional images that make it possible to view the fluid along at least one direction selected from (a) a moving direction and (b) a diffusion direction of the fluid.

5. The image processing apparatus according to claim 2, wherein the label region is set in an imaging region.

6. The image processing apparatus according to claim 2, wherein the index values are derived based on position information of the label region.

7. The image processing apparatus according to claim 2, wherein, after a morphological region in which the fluid is flowing and which corresponds to anatomical morphology is specified within the images, the index values are derived by using a straight line or a curve that passes through the morphological region.

8. The image processing apparatus according to claim 2, wherein the index values are derived by using one of the following:
    a position of a pixel that has a longest distance from a reference position specified in the images;
    a position of a pixel that has a longest distance from the reference position, the distance being calculated along a straight line or a curve; and
    a position of a pixel at a gravity point within the region.

9. The image processing apparatus according to claim 1, wherein the fluid region in the images that have been acquired along a time series is specified in accordance with a temporal change in image signal intensity.

10. The image processing apparatus according to claim 1, wherein
    the fluid region in the images that have been acquired is specified along a time series, and the index values are derived based on a feature value at successive times of each successive position of the specified fluid region.

11. The image processing apparatus according to claim 1, wherein the fluid region in the images that have been acquired is specified along a time series, and the index values derived along the time series is displayed on a display along the time series.

12. The image processing apparatus according to claim 11, wherein the executed program instructions cause display, of (a) an image corresponding to at least one of the time phases from among the images corresponding to the plurality of time phases and (b) a feature value used for deriving the index values so as to be superimposed on the displayed image.

13. The image processing apparatus according to claim 12, wherein the display displays the feature value superimposed on the image using a predetermined symbol.

14. The image processing apparatus according to claim 12, wherein the display displays the feature value in a specified color superimposed on the image.

15. The image processing apparatus according to claim 1, wherein:

execution of said computer program instructions effects display of the derived index on a display includes a graphic displayed which includes a first axis and a second axis, the first axis expressing a position of the fluid or an area size of the fluid, the second axis expressing a time direction.

16. The image processing apparatus according to claim 1, wherein the program instructions, when executed:

display the derived velocity in a superimposed manner on the graph.

17. An image processing apparatus comprising:

at least one computer connected to communicate with memory storing (a) a plurality of magnetic resonance images acquired from a subject representing anatomical structures having fluid portions therewithin and (b) executable computer program instructions which, when executed by said at least one computer;

specify a cerebrospinal fluid (CSF) region which is a region corresponding to a CSF portion of a subject in a plurality of magnetic resonance images that have been acquired by applying a labeling pulse to a label region and that are mutually related by having been acquired while imaged CSF fluid therein was moving;

derive a plurality of index values and derive a change in CSF velocity based on the index values, wherein the index values include at least one of a position of a specific part of the specified CSF region in the images and an area size of the specified CSF region in the images; and display an image showing a graph plotting the index values against time and the change in CSF velocity during the time data defining the images was acquired.

* * * * *